United States Patent
Ribi (12)

(10) Patent No.: US 10,302,508 B2
(45) Date of Patent: May 28, 2019

(54) CO-TOPO POLYMERIC COMPOSITIONS, DEVICES AND SYSTEMS FOR CONTROLLING THRESHOLD AND DELAY ACTIVATION SENSITIVITIES

(71) Applicant: Segan Industries, Inc., Burlingame, CA (US)

(72) Inventor: Hans O. Ribi, Hillsborough, CA (US)

(73) Assignee: Segan Industries, Inc., Burlingame, CA (US)

( * ) Notice: Subject to any disclaimer, the term of this patent is extended or adjusted under 35 U.S.C. 154(b) by 0 days.

(21) Appl. No.: 15/860,464

(22) Filed: Jan. 2, 2018

(65) Prior Publication Data

US 2018/0180492 A1    Jun. 28, 2018

Related U.S. Application Data

(63) Continuation of application No. 14/860,158, filed on Sep. 21, 2015, now Pat. No. 9,857,236, which is a
(Continued)

(51) Int. Cl.
| | |
|---|---|
| *G01K 11/12* | (2006.01) |
| *C09B 57/10* | (2006.01) |
| *C08F 238/02* | (2006.01) |
| *C09K 19/54* | (2006.01) |
| *G01N 21/78* | (2006.01) |

(Continued)

(52) U.S. Cl.
CPC ............ *G01K 11/12* (2013.01); *C08F 238/02* (2013.01); *C09B 57/10* (2013.01); *C09B 67/0013* (2013.01); *C09K 19/542* (2013.01); *G01D 7/005* (2013.01); *G01K 1/02* (2013.01); *G01K 3/04* (2013.01); *G01N 21/78* (2013.01)

(58) Field of Classification Search
CPC ................................. G01K 11/12; G01K 11/16
USPC ......................................................... 252/408.1
See application file for complete search history.

(56) References Cited

U.S. PATENT DOCUMENTS

| | | | |
|---|---|---|---|
| 3,277,198 A | 10/1966 | Holm et al. | |
| 3,501,297 A * | 3/1970 | Cremeans | ............... C07C 57/24 250/474.1 |

(Continued)

FOREIGN PATENT DOCUMENTS

| | | |
|---|---|---|
| WO | 1999039167 A1 | 8/1999 |
| WO | 2002000920 A2 | 1/2002 |

(Continued)

*Primary Examiner* — Tae H Yoon
(74) *Attorney, Agent, or Firm* — Khin K. Chin; Bret E. Field; Bozicevic, Field & Francis LLP

(57) ABSTRACT

Co-topo-polymeric indicator compositions and methods for making and using the same are provided. Indicator compositions of the invention include a polymer and undergo a color change, which may be reversible or irreversible, in response to an applied stimulus, e.g., temperature. Aspects of methods of producing the compositions include setting a fluid co-topo-polymeric precursor composition into a solid product and then subjecting the solid product (either immediately or after a delay period) to polymerizing conditions to produce the desired indicator composition. Also provided are indicator devices that include the indicator compositions of the invention. The compositions of the invention find use in a variety of different applications.

21 Claims, 21 Drawing Sheets

Related U.S. Application Data continuation of application No. 14/086,380, filed on Nov. 21, 2013, now Pat. No. 9,164,041, which is a continuation of application No. 13/458,905, filed on Apr. 27, 2012, now Pat. No. 8,617,900, which is a continuation of application No. 12/505,405, filed on Jul. 17, 2009, now Pat. No. 8,187,892.

(60) Provisional application No. 61/082,792, filed on Jul. 22, 2008, provisional application No. 61/082,118, filed on Jul. 18, 2008.

(51) Int. Cl.
*C09B 67/08* (2006.01)
*G01D 7/00* (2006.01)
*G01K 3/04* (2006.01)
*G01K 1/02* (2006.01)

(56) References Cited

U.S. PATENT DOCUMENTS

| | | | |
|---|---|---|---|
| 4,384,980 A | 5/1983 | Patel | |
| 4,705,742 A * | 11/1987 | Lewis | G03C 7/46 430/296 |
| 4,892,677 A | 1/1990 | Prezioci et al. | |
| 5,085,801 A | 2/1992 | Thierry et al. | |
| 6,046,455 A | 4/2000 | Ribi et al. | |
| 6,103,459 A | 8/2000 | Diel | |
| 6,241,913 B1 | 6/2001 | Angelopoulos et al. | |
| 6,465,791 B1 | 10/2002 | Ribi et al. | |
| 6,607,744 B1 | 8/2003 | Ribi | |
| 6,787,108 B2 * | 9/2004 | Ribi | G01N 31/229 116/206 |
| 6,866,863 B2 | 3/2005 | Ribi | |
| 7,371,511 B2 * | 5/2008 | Koecher | C08G 18/4841 428/500 |
| 8,269,042 B2 | 9/2012 | Baughman et al. | |
| 2002/0025490 A1 | 2/2002 | Shchegolikhin et al. | |
| 2003/0034475 A1 | 2/2003 | Ulincy et al. | |
| 2003/0103905 A1 | 6/2003 | Ribi | |
| 2003/0143188 A1 | 7/2003 | Ribi | |
| 2004/0072933 A1 | 4/2004 | Shustack | |
| 2005/0109984 A1 | 5/2005 | Potyrailo et al. | |
| 2007/0251912 A1 | 11/2007 | Sixou et al. | |
| 2007/0273951 A1 | 11/2007 | Ribi | |
| 2007/0275371 A1 | 11/2007 | Sim et al. | |

FOREIGN PATENT DOCUMENTS

| | | |
|---|---|---|
| WO | 2003037391 A1 | 5/2003 |
| WO | 2004090629 A2 | 10/2004 |
| WO | 2005028524 A1 | 3/2005 |
| WO | 2005029163 A1 | 3/2005 |
| WO | 2005036109 A2 | 4/2005 |
| WO | 2005123023 A1 | 12/2005 |
| WO | 2007111702 A2 | 10/2007 |
| WO | 2008051550 A2 | 5/2008 |
| WO | 2008079357 A2 | 7/2008 |

* cited by examiner

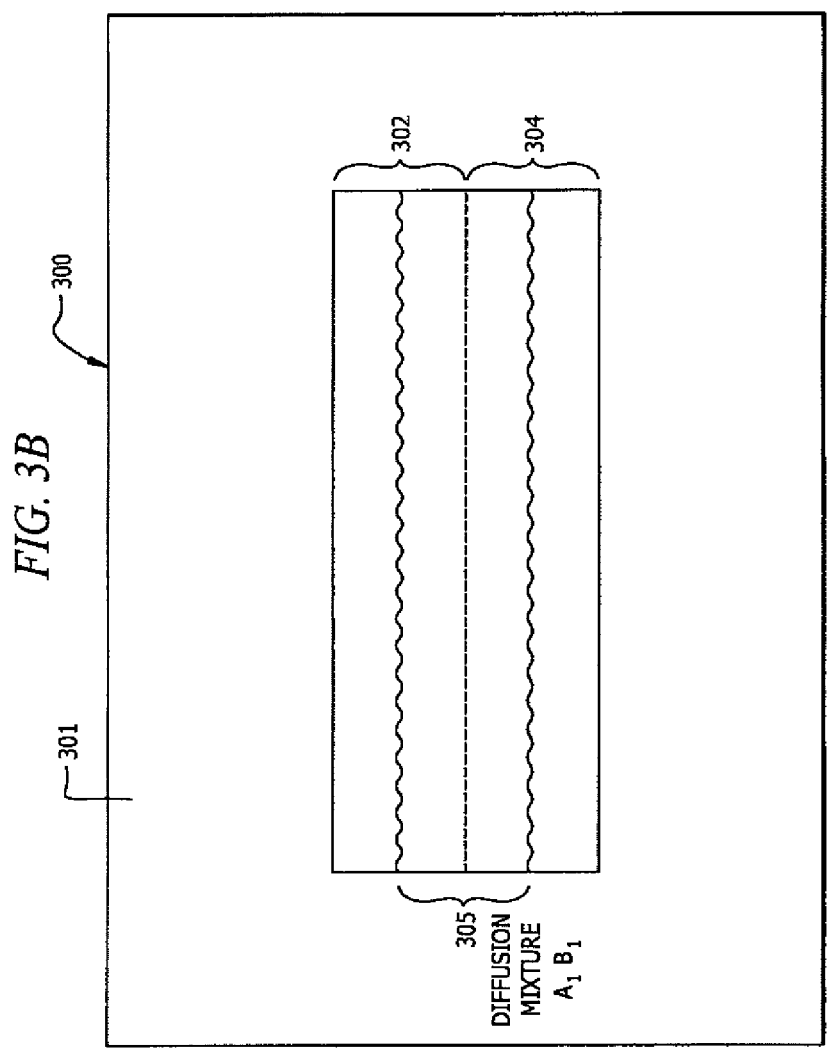

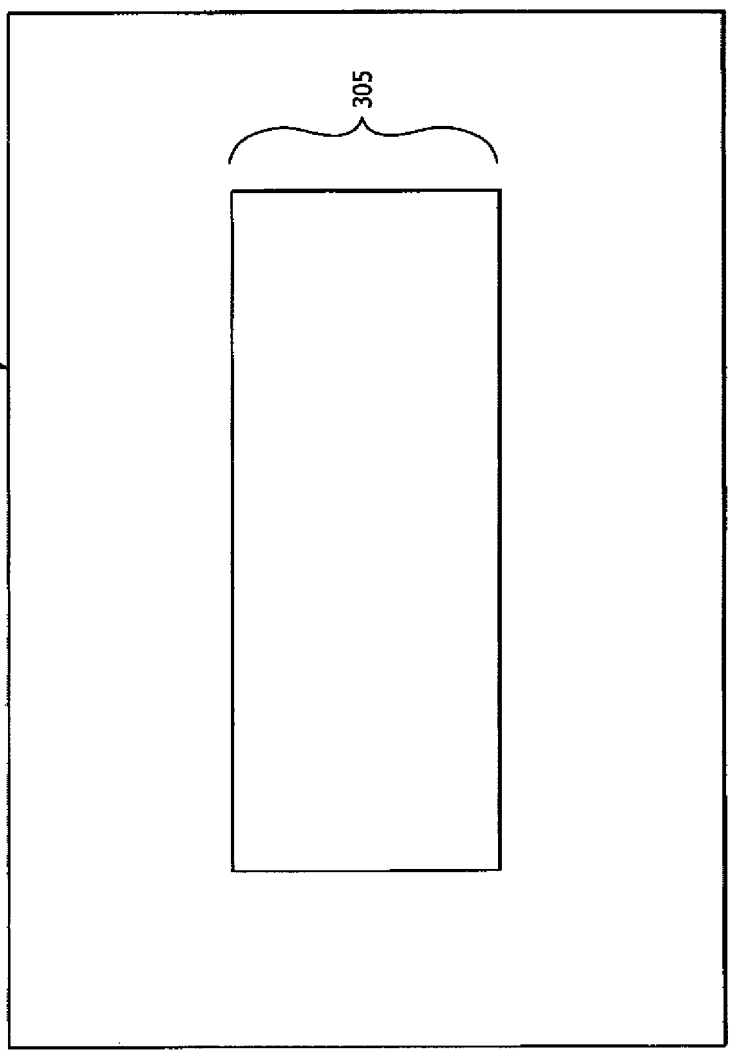

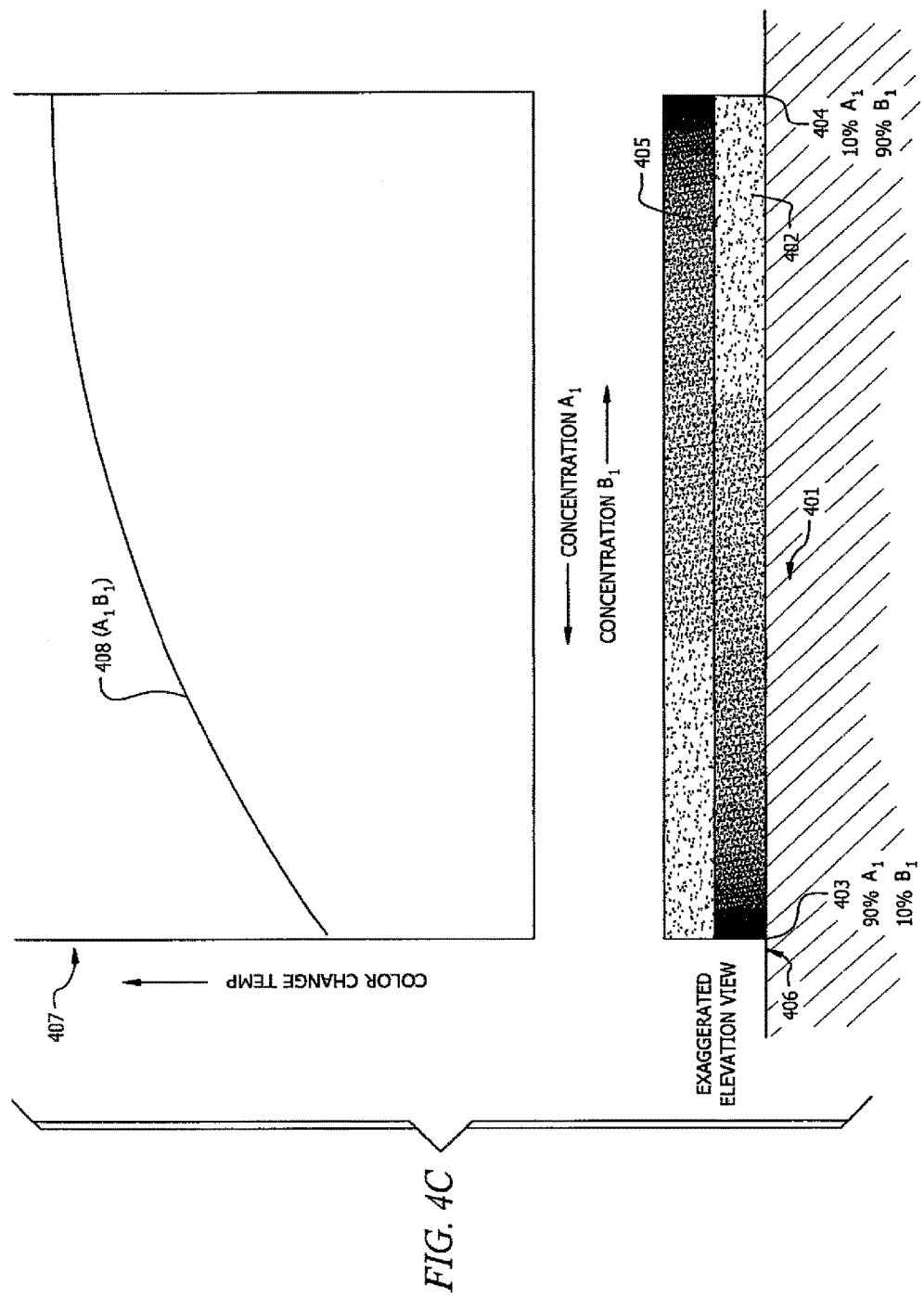

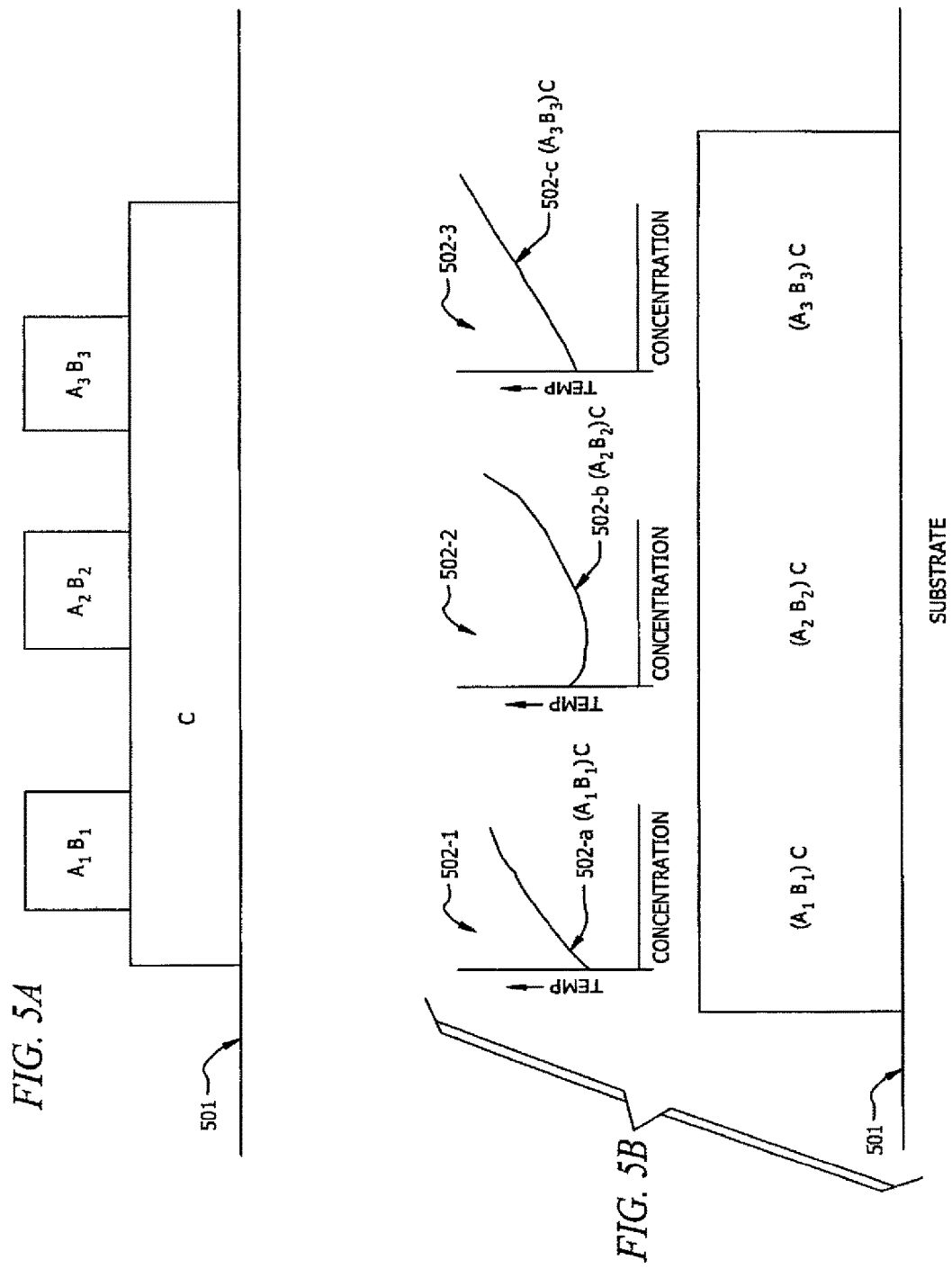

CO-TOPO POLYMERIC COMPOSITIONS, DEVICES AND SYSTEMS FOR CONTROLLING THRESHOLD AND DELAY ACTIVATION SENSITIVITIES

CROSS-REFERENCE TO RELATED APPLICATIONS

This application is a continuation of U.S. patent application Ser. No. 14/860,158 filed Sep. 21, 2015, now U.S. Pat. No. 9,857,236, which is a continuation of U.S. patent application Ser. No. 14/086,380 filed Nov. 21, 2013, now U.S. Pat. No. 9,164,041, which is a continuation of U.S. patent application Ser. No. 13/458,905 filed Apr. 27, 2012, now U.S. Pat. No. 8,617,900, which is a continuation of U.S. patent application Ser. No. 12/505,405 filed Jul. 17, 2009, now U.S. Pat. No. 8,187,892. Pursuant to 35 U.S.C. § 119 (e), this application claims priority to the filing dates of U.S. Provisional Patent Application Ser. No. 61/082,118 filed Jul. 18, 2008 and U.S. Provisional Patent Application Ser. No. 61/082,792 filed Jul. 22, 2008; the disclosures of which applications are herein incorporated by reference.

INTRODUCTION

Perishable products such as foods, beverages and pharmaceuticals have to be stored in controlled environments prior to consumption or use, if the quality and safety of these products are to be assured. The suitability of these perishable products for sale, consumption or use can be compromised by exposure to heat, light, humidity and micro-organisms. Consequently, the supply chain for these perishable products has to be controlled in a manner that ensures that the series of conditions, in the chain of supply, to which the products are exposed, meet established standards.

For example, a supply chain where the temperature is controlled is known as a cold chain. A cold chain seeks to control the temperature of products, from production to purchase or consumption, in a particular range, for example 5 to 10° C. A cold chain is often necessary for perishable products because most of these products deteriorate with a rise in temperature. An important point to note with regard to a cold chain is that once the "link" is broken, that "broken link" cannot be remedied. For example, if milk requires storage at a temperature of 5 to 10° C., and a container of milk was exposed to a temperature of 25° C. for two hours, then subsequent re-cooling of that container of milk to between 5 to 10° C. does not correct the problems caused by the two hours of exposure to the higher temperature. The prolonged high temperature has irreversibly spoiled the milk. The history of environmental conditions, such as temperature, to which a product has been exposed is therefore critical in informing a consumer that a product, that is about to be consumed or used, is safe or of good quality.

Currently, consumers are not provided with an accurate indication that a product has been stored properly in the supply chain leading to the consumer. At best, the consumer is provided with a shelf-life. Further, through thermometers in the product display, the consumer can observe that, when purchased, the product was in proper storage conditions. The consumer has nothing to rely on, however, to be assured that the product was properly stored at every stage in the supply chain prior to reaching the final point of sale. Moreover, shelf-life, which is heavily relied on in the industry, is dependent on the whether proper storage conditions are maintained in the supply chain.

There have been some products and systems devised, for use by non-consumer parties, in the chain of supply, to indicate whether products have been mishandled. These systems however, do not directly inform the end consumer. Even for the non-consumer parties to which these systems are applicable, the systems have been inadequate for several reasons. For example, bar codes have been used for tracking each stage of handling. This system involves asking individuals to confirm that goods have been delivered in good shape. However, this system is subjective because it is based on parties documenting whether their own activities have been proper. In another system, electronic devices called trip trackers are placed in containers carrying goods to track the temperature of the containers. However, this system is expensive and ineffective. For example, the temperature in the location where the electronic equipment is located may be adequate but there may be other sections of the container at an inadequate temperature. There exists a need, therefore, for systems and products that can economically and reliably indicate whether a perishable product has been exposed to conditions detrimental to the perishable product.

SUMMARY

Co-topo-polymeric indicator compositions and methods for making and using the same are provided. Indicator compositions of the invention include a polymer and undergo a color change, which may be reversible or irreversible, in response to an applied stimulus, e.g., temperature. Aspects of methods of producing the compositions include setting a fluid co-topo-polymeric precursor composition into a solid product and then subjecting the solid product to polymerizing conditions (e.g., immediately or after some delay) to produce the desired indicator composition. Also provided are indicator devices that include the indicator compositions of the invention. The compositions of the invention find use in a variety of different applications.

BRIEF DESCRIPTION OF THE FIGURES

FIGS. 3A-C show the printing of inks with single monomers to create a mixture of monomers on a substrate, where the mixture of monomers is a co-topo-polymeric composition that may be polymerized to produce an indicator.

FIGS. 4A-4C show how precursor compositions are applied to create a strip of ink with portions that change color at different temperatures.

FIGS. 5A-B show how precursor compositions may be applied to create a printed product with multiple color change temperature-concentration curves.

DETAILED DESCRIPTION

Figure 1:
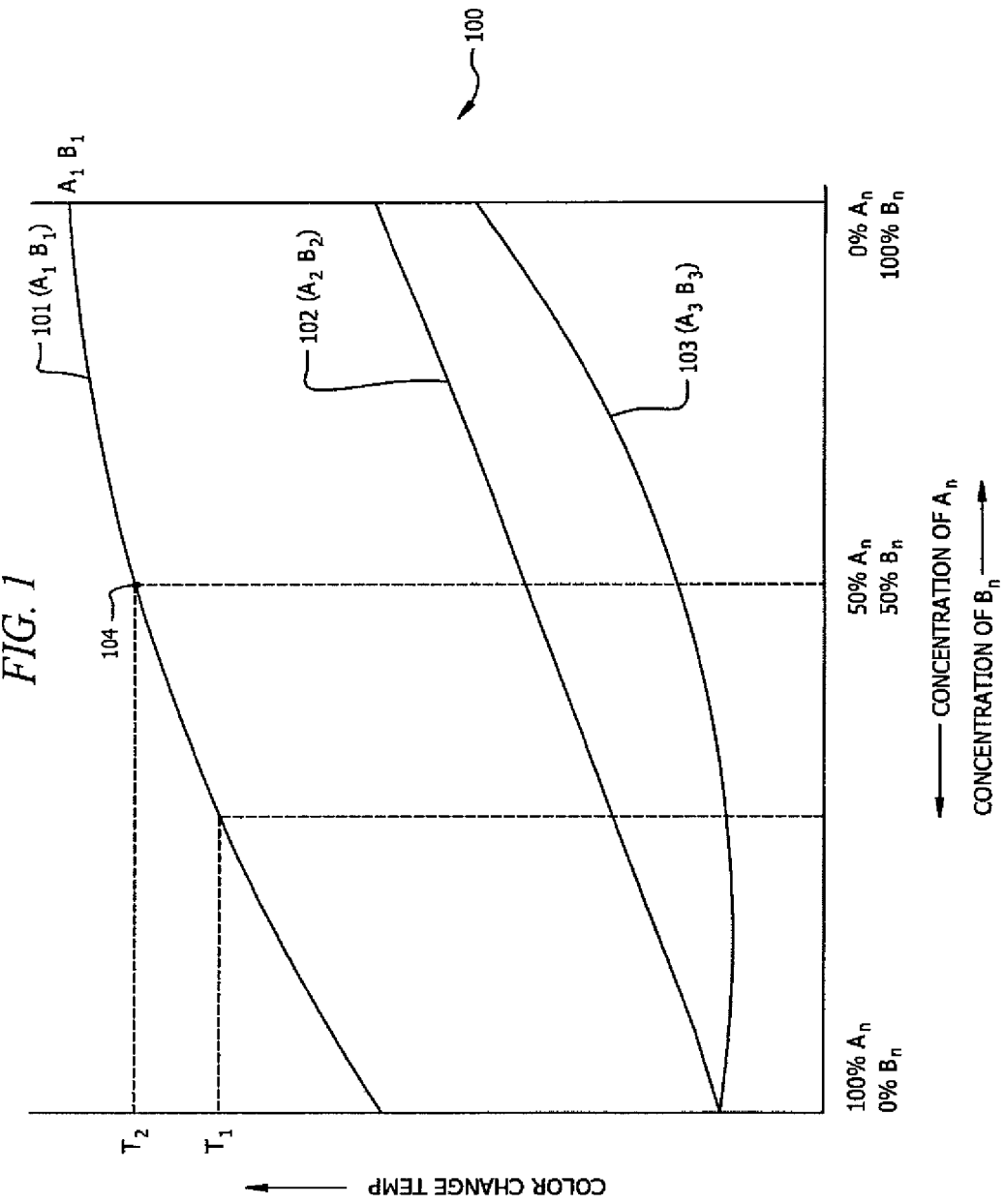
FIG. 1 is a graph showing color change temperature plotted against different co-topo-polymeric indicator compositions that are made from different precursor compositions having differing concentrations of one or more miscible monomers.

Co-topo-polymeric indicator compositions and methods for making and using the same are provided. Indicator compositions of the invention include a polymer and undergo a color change, which may be reversible or irreversible, in response to an applied stimulus, e.g., temperature. Aspects of methods of producing the compositions include setting a fluid co-topo-polymeric precursor composition into a solid product and then subjecting the solid product to polymerizing conditions to produce the desired indicator composition. Also provided are indicator devices that include the indicator compositions of the invention. The compositions of the invention find use in a variety of different applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the various aspects of the invention, the co-topo-polymeric indicator compositions and methods for making the same are reviewed first in greater detail, followed by a review of various applications in which the indicator compositions find use.

Co-Topo-Polymeric Indicator Compositions

As reviewed above, aspects of the invention include co-topo-polymeric indicator compositions. Co-topo-polymeric indicator compositions are compositions that change color in response to an applied stimulus, such as a temperature. The co-topo-polymeric indicator compositions are characterized in that they change color in response to known or predetermined applied stimulus, such that the stimulus whose application changes color of the composition is known. High, medium, or low temperature/triggering co-topo-polymeric color change compositions are provided by the invention.

The co-topo-polymeric compositions are polymeric compositions that they are produced via polymerization of one or more monomeric components of a precursor composition. As such, precursor compositions of the invention are compositions that include one or more distinct monomer compounds, where when two or more distinct monomeric compounds of different structure are present, these two or more distinct monomeric compounds may be analogs that differ structurally in one or more elements, a combination of elements, etc. The precursor compositions may have various ratios of distinct monomeric compounds, such as monomeric analogs, and may include one or more effector additives, e.g., that find use during co-crystallization, or other agents. Where a single monomeric analog is present, a co-mixing analog may also be present. The color-changing aspect of the co-topo-polymeric indicator compositions may be irreversible or reversible, such that the triggering transitions of the indicator compositions can be irreversible or reversible.

Co-topo-polymeric compositions of the invention satisfy an immediate and growing need to rapidly and accurately develop, produce and supply specific visual or machine readable temperature indicators that cover a very broad temperature range. Temperature indicating compositions of invention may be configured to reliable change color a discrete temperature ranging over a wide temperature range, where the triggering temperature that causes a given indicator composition to change color may be any specific temperature ranging from below −50° F. to above 300° F., such as in the range of −40° F. to 200° F., including in the range of −30° F. to 150° F., e.g., in the range of −20° F. to 100° F. In some instances, low temperature indicators are of interest, such as indicators that change color at a triggering temperature ranging from −50° F. to above 60° F., such as −40° F. to above 50° F., including −20° F. to above 32° F.

The indicator compositions of the invention may be employed directly on an item of interest (e.g., a food item, etc) or on a substrate, where the substrate is in turn associated with the item of interest, e.g., as described in greater detail below. Where desired, indicator compositions may be coated with a protective coating, e.g., PVP.

Device and indicators for various product applications can include single temperature settings and/or a plurality of individual temperature settings. By way of example, but not limitation, indicators can include 1 to over 100 temperature zones comprised with specified co-topo-polymeric compositions with pre-determined temperature settings. The number of temperature zones may vary, ranging from 1 to over 50 independent or plural temperature zones, such as from 1 to 20 temperature zones, including from 1 to 10 temperature event settings. The number of temperature settings selected to utilize ratios of co-topo-polymeric compositions will depend on the product application of interest.

Co-topo-polymeric indicator compositions are polymeric compositions that are prepared from co-topo-polymeric precursor compositions that include one or more monomeric compounds, where the precursor compositions may include one or more additional components, e.g., as described in greater detail below.

Co-Topo-Polymeric Precursor Compositions

Formulations of co-topo-polymeric precursor compositions for selected indicator and product types can be determined both experimentally and by physical chemical diagrams, can be achieved by choosing molecular features and attributes including but not limited to: hydrocarbon chain length, strait or branched chains, pure hydrocarbon chains or substituted chains, position of the diacetylenic moiety along the length of a hydrocarbon chain, number of diacetylenic moieties in a given molecular analog, number or hydrocarbon chains containing diacetylenic moieties comprising the molecular analog, the presence or absence of hydrophilic substituents, the presence of hydrogen bonding groups including, but not limited to esters, amide groups, sulfhydral groups, quaternary charged groups, other charged species, chiral and achiral groups, appended groups, multiple or single hydrogen bonding groups, non-hydrogen bonding analogs, polar and non-polar head groups, head groups with substituents or are unsubstituted, head group side chains, bis-coupled analogs where coupling is direct or through a linkers, bis molecules with different molecular compositions, and the like.

As described herein, a major enabling advantage of co-topo-polymeric compositions is that a small number of monomer structural analogs when mixed and combined together utilizing measured phase diagrams, phase curves, and/or empirical testing can be admixed and formulated to cover a wide range of product applications. Importantly and by way of example, careful adjustment of molecular, molar or weight ratios of only a selected number like-kind or related molecular analogs can be utilized to cover a temperature range of over 200° F. Either by experiment or by phase diagram prediction, co-topo-polymeric compositions can be formulated and adjusted in ratios using only 2-3 analogs to cover create indicators that cover a temperature range of over 100° F.

As reviewed in greater detail below, the precursor and indicator compositions of the invention may be configured in a variety of formats, such as fluid formats (e.g., for printing on a substrate, e.g., with a printing device or with a hand-held marker), malleable solid formats, e.g., putties, non-malleable solid formats, etc.

Diacetylenic Precursor Compositions

In some embodiments, precursor compositions of the invention include two or more diacetylenic monomer analogs, where these diacetylenic monomer analogs differ from each other in one or more ways (e.g., as described above), such as in monomer chain hydrocarbon chain length (e.g., 10 to 30 carbon atoms long, such as 15 to 30 carbon atoms long, including 20 to 25 carbon atoms long), head-group structure (e.g., ester, amide, etc.), bond positioning, appendages, chirality, related features, and/or combinations thereof. Asymmetric acyl:non-acyl groups appended to each end of the diacetylenic group are of interest in certain embodiments due to the versatile nature and flexibility of corresponding analogs that can be generated by chemical modification and importantly due to the ability to modify the temperature transition temperature of a particular analog.

Specific combinations of diacetylenic monomers that may be present in a given co-topo-polymeric precursor composition include the following specific mixtures of two or three different diacetylenic monomers, as provided in the tables below. (In the nomenclature appearing in the following tables, "Cn", where n is an integer ranging from 19 to 30, denotes the length of the carbon chain of the diacetylenic monomer. The numbers appearing before Cn denote the sites of unsaturation in the diacetylenic monomer. Accordingly, Me-10,12-C21 refers to the methyl ester of 10,12-heneicosadiynoic acid while 10,12-C21 refers to 10,12-heneicosadiynoic acid.)

Of interest are dual monomer precursor compositions that are made up of two different alkyl-ester diacetylenic monomers, where specific examples of such precursor compositions are shown in Table 1, below.

TABLE 1

Dual Monomer Precursor Compositions of Alkyl Ester Diacetylenic Monomers
Me = Methyl

| | | |
|---|---|---|
| Me-10,12-C18:Me-10,12-C19 | Me-10,12-C19:Me-10,12-C20 | Me-10,12-C20:Me-10,12-C21 |
| Me-10,12-C18:Me-10,12-C20 | Me-10,12-C19:Me-10,12-C21 | Me-10,12-C20:Me-10,12-C22 |
| Me-10,12-C18:Me-10,12-C21 | Me-10,12-C19:Me-10,12-C22 | Me-10,12-C20:Me-10,12-C23 |
| Me-10,12-C18:Me-10,12-C22 | Me-10,12-C19:Me-10,12-C23 | Me-10,12-C20:Me-10,12-C24 |
| Me-10,12-C18:Me-10,12-C23 | Me-10,12-C19:Me-10,12-C24 | Me-10,12-C20:Me-10,12-C25 |
| Me-10,12-C18:Me-10,12-C24 | Me-10,12-C19:Me-10,12-C25 | Me-10,12-C20:Me-10,12-C26 |
| Me-10,12-C18:Me-10,12-C25 | Me-10,12-C19:Me-10,12-C26 | Me-10,12-C20:Me-10,12-C27 |

TABLE 1-continued

Dual Monomer Precursor Compositions of Alkyl Ester Diacetylenic Monomers
Me = Methyl

| | | |
|---|---|---|
| Me-10,12-C18:Me-10,12-C26 | Me-10,12-C19:Me-10,12-C27 | Me-10,12-C20:Me-10,12-C28 |
| Me-10,12-C18:Me-10,12-C27 | Me-10,12-C19:Me-10,12-C28 | Me-10,12-C20:Me-10,12-C29 |
| Me-10,12-C18:Me-10,12-C28 | Me-10,12-C19:Me-10,12-C29 | Me-10,12-C20:Me-10,12-C30 |
| Me-10,12-C18:Me-10,12-C29 | Me-10,12-C19:Me-10,12-C30 | |
| Me-10,12-C18:Me-10,12-C30 | | |
| Me-10,12-C21:Me-10,12-C22 | Me-10,12-C22:Me-10,12-C23 | Me-10,12-C23:Me-10,12-C24 |
| Me-10,12-C21:Me-10,12-C23 | Me-10,12-C22:Me-10,12-C24 | Me-10,12-C23:Me-10,12-C26 |
| Me-10,12-C21:Me-10,12-C24 | Me-10,12-C22:Me-10,12-C25 | Me-10,12-C23:Me-10,12-C27 |
| Me-10,12-C21:Me-10,12-C25 | Me-10,12-C22:Me-10,12-C26 | Me-10,12-C23:Me-10,12-C28 |
| Me-10,12-C21:Me-10,12-C26 | Me-10,12-C22:Me-10,12-C27 | Me-10,12-C23:Me-10,12-C29 |
| Me-10,12-C21:Me-10,12-C27 | Me-10,12-C22:Me-10,12-C28 | Me-10,12-C23:Me-10,12-C30 |
| Me-10,12-C21:Me-10,12-C28 | Me-10,12-C22:Me-10,12-C29 | |
| Me-10,12-C21:Me-10,12-C29 | Me-10,12-C22:Me-10,12-C30 | |
| Me-10,12-C21:Me-10,12-C30 | | |
| Me-10,12-C24:Me-10,12-C25 | Me-10,12-C25:Me-10,12-C26 | Me-10,12-C26:Me-10,12-C27 |
| Me-10,12-C24:Me-10,12-C26 | Me-10,12-C25:Me-10,12-C27 | Me-10,12-C26:Me-10,12-C28 |
| Me-10,12-C24:Me-10,12-C27 | Me-10,12-C25:Me-10,12-C28 | Me-10,12-C26:Me-10,12-C29 |
| Me-10,12-C24:Me-10,12-C28 | Me-10,12-C25:Me-10,12-C29 | Me-10,12-C26:Me-10,12-C30 |
| Me-10,12-C24:Me-10,12-C29 | Me-10,12-C25:Me-10,12-C30 | |
| Me-10,12-C24:Me-10,12-C30 | | |
| Me-10,12-C27:Me-10,12-C28 | Me-10,12-C28:Me-10,12-C29 | |
| Me-10,12-C27:Me-10,12-C29 | Me-10,12-C28:Me-10,12-C30 | |
| Me-10,12-C27:Me-10,12-C30 | | |

Also of interest are triple monomer precursor compositions that are made up of three different alkyl-ester diacetylenic monomers, where specific examples of such precursor compositions are shown in Table 2, below.

TABLE 2

Triple Monomer Precursor Composition
of Alkyl Ester Diacetylenic Monomers
Me = Methyl; Et = Ethyl; Pr = Propyl

| | | |
|---|---|---|
| Me-10,12-C18 | Me-10,12-C21 | Me-10,12-C23 |
| Et-10,12-C18 | Et-10,12-C21 | Et-10,12-C23 |
| Pr-10,12-C18 | Pr-10,12-C21 | Pr-10,12-C23 |
| Me-10,12-C25 | Me-10,12-C27 | Me-5,7-C12 |
| Et-10,12-C25 | Et-10,12-C27 | Et-5,7-C12 |
| Pr-10,12-C25 | Pr-10,12-C27 | Pr-5,7-C12 |
| Me-5,7-C14 | Me-5,7-C16 | Me-5,7-C18 |
| Et-5,7-C14 | Et-5,7-C16 | Et-5,7-C18 |
| Pr-5,7-C14 | Pr-5,7-C16 | Pr-5,7-C18 |
| Me-5,7-C20 | Me-5,7-C22 | Me-5,7-C24 |
| Et-5,7-C20 | Et-5,7-C22 | Et-5,7-C24 |
| Pr-5,7-C20 | Pr-5,7-C22 | Pr-5,7-C24 |

The above tables merely provide examples of the different combinations of diacetylenic monomers that may be present in a given indicator precursor composition.

In preparing an indicator composition from a precursor composition, e.g., as described above, the monomers be admixed in a dissolved state, co-crystallized and co-topopolymerized in the solid state of the indicator composition. Mixed systems may or may not require that each mixed analog in a composition be independently polymerizable, so long as the resulting combination is polymerizable. The polymerization step may occur immediately after mixing or after some time delay, such that polymerization (which activates the indicator) occurs at some point following application of the precursor composition to a substrate or item of interest to be monitored.

Mixed compositions can be formulated to significantly alter the properties of the final system compared with the properties of a pure analog utilized to formulate the final system. By way of example but not limitation, two low temperature monomers such as the methyl ester of 10, 12-heneicosadiynoic acid (Me-10,12-C21) and the propyl ester of 10, 12-heneicosadiynoic acid (Pr-10,12-C21) can be mixed in varying ratios to achieve discrete threshold melting transition in the monomeric state, discrete polymerization temperatures, discrete color change temperature transitions, and selective sensitivity ranges to other color change stimuli, such as but not limited to: friction, chemical triggering, solvent triggering, and/or other environmental stimuli. Ratios can range from a fraction of a mole percent of one component to a fraction of a mole percent of the other component. Both eutectic and non-eutectic mixtures can be achieved with accurate measurement. The color change triggering transition can be lowered by 1 to greater than 50° F. or more as compared with the temperature transition of a single component (e.g. the methyl ester of 10, 12-heneicosadiynoic acid).

Of interest in certain embodiments are temperature downshifted esters of corresponding carboxylic acids in which the temperature transition of a long chain carboxylic acid monomer can be down-shifted in temperature by between 10 to 100° F. depending on the initial carboxylic acid structure and the esterification modification employed.

Further temperature down-shifting can be accomplished by admixing selected ratios of different ester types to correspondingly reduce the initially chemically downshifted structures to further mixed downshifted compositions. The effective combination of chemical and mixed downshifting of certain embodiments brings an initial long chain carboxylic acid structure from a temperature transition of greater than 180° F. to lower than 0° F.

As such, aspects of the invention include non-pure alkyl forms of diacetylenic monomers that exhibit a highly controllable irreversible thermochromic property. In specific embodiments, long chain high temperature analogs such as 10,12-einecosadiynoic acid, 10, 12-tricosadiynoic acid, 10,12-pentacosadiynoic acid are dramatically down-shifted in their thermochromic transition temperature from a range of 100° F. to 200° F. down to −40° F. to 90° F. As such, embodiments of the indicator compositions include compositions that have a temperature trigger ranging from −40° F. to 90° F.

Diacetylenic monomers of interest may be produced via a simple esterification process utilizing a suitable alkanol, such as methanol, ethanol, n-propanol, n-butanol, n-pentanol, and extended longer chain alcohols as well as branched alcohols that significantly and reproducibly lowers the thermochromic transition of the parent compound as well as extinguishes any reversible hysteresis rendering the thermochromic properties entirely irreversible. Likewise, ratios of mixed compounds are selected to generate a pre-determined temperature setting that can be predicted based on the specific ratio between the various diacetylenic monomers in the precursor composition.

The precursor compositions of the present invention are distinguished from pure hydrocarbon based systems which lack the elements of non-hydrocarbon interactivity, where precursor compositions of the present invention may exhibit interactions of one or more of hydrophilic and hydrophobic head groups, hydrogen bonding substituents, mesophasic side chains, side-chain control elements, with mixed hydrocarbon compositions compared with amphiphylic-based mixed compositions and the like.

Co-topo-polymeric precursor compositions of certain embodiments may exhibit an enriched and accelerated degree of polymerization, as compared to pure compositions. Doping one component of a co-topo-polymeric component with another like-kind element promotes the degree of polymerization and rapidity of polymerization compared with pure individual compositions. Admixed co-topo-polymeric components (e.g., diacetylenic monomers) can be in pairs or more complex mixtures of 3 or more components. Mixed compositions can be produced that create blends of from 2 to more than 50 individual monomer types, such as 2 to 10 types, including 2 to 4 different monomer types. Ratios of two components can range from 0.001% of a first component to 99.999% of a second component, such as 0.01 of a first component to 99.99% of a second component, including from 0.1% of a first component to 99.9% of a second component, e.g., 1% of a first component to 99% of a second component. The exact ratio of each component will be selected based on the desired temperature setting and characteristics of the intended product application for the composition.

Single chain monomers, dual chain monomers or higher order chain monomers can be used alone or in combinations here within in the prescribed ratios. The mixed co-topo polymeric precursor composition containing only single chain monomers or mixtures of multiple chain monomers with single chain monomers will be selected based on the product application of interest.

Vehicle

In addition to the one or more monomers, e.g., as described above, the precursor compositions may include a vehicle that is made of up one or more discrete components. As such, monomers of precursor compositions for co-topo-polymeric indicator compositions can be applied to a surface (such as a substrate or directly to an item to be monitored) neat or in combination with various vehicles, such as where the compositions are applied in oil forms (including re-settable oil compositions, e.g., with a security feature of residual indicating polymer), in microencapsulated forms, in aqueous coating matrix compositions (including water-based resins), in solvent-based coating compositions, in emulsions, with protective over-coatings (e.g., PVP), in soluble plastic matrix resins, in wax matrix compositions, a range of different organic or polymeric matrix compositions, rubbers, thermal set resins, epoxies, varnishes, printing inks and binders and the like.

Non-Temperature Triggering Agent

Co-topo-polymeric compositions may be formulated for detection of triggering agents alternative to temperature. Lipids, oils fats, greases, selected reactive chemistries, ionic strength changes, solvents, gases, pH changes and the like can be used alone or in combination with a temperature threshold event as triggering stimuli to induce a color change event in a co-topo-polymeric indicator composition of the invention. Triggering agents can initiate a color change event in the co-topo-polymeric indicator composition when the agent is present in a 1:100,000 and 100,000 molar ratio between the triggering agent and the co-topo-chemical polymeric composition. In some instances, the ratios range from 1:10,000 and 10,000:1, such as from 1:1,000 and 1,000:1, and including from 1:100 and 100:1.

Property Shifting Additives:

Cholesteric liquid crystals can be added as augmenting agents that affect the properties of oil based diacetylenic monomers and mixed monomer systems. The nematic and smectic phase crystallization properties of liquid crystals can be utilized to affect the topo-chemical crystallization/polymerization properties of diacetylenic compositions.

Various oils including organic, natural, inorganic, and synthetic oils can be added to diacetylenic compositions to up temperature shift or down temperature shift the original diacetylenic composition's intrinsic temperature threshold. Oils can include, but are not limited to corn oil, various vegetables oils, nut oils, root oils, herbal oils, paraffin oils, greases, animal fats, natural extract oils, flavor based oils, aromatic based oils, industrial oils, and the like can be added to assist in modulating the temperature setting of an co-topo-polymeric composition or pure diacetylenic composition. One or more different oils may be present, as desired.

Oil based modulating additives or the like can be added at percentages that promote a desired temperature threshold response of interest. Modulating additives can be added and can be effective from 0.0001% by weight to a soluble monomer composition to greater than 90% by weight. In certain instances, modulating additives are present in amounts ranging from between 0.001% up to 80% by weight, such as from between 0.01% up to 70% by weight, including from between 0.1% and up to 50% by weight, e.g., from between 1% and 25% by weight.

Co-Topo-Polymeric Composition Formats

Co-topo-polymeric compositions, including both precursor and indicator compositions, may be configured in a variety of formats, including on the surfaces of various substrates, in combination with additional sensors and agents, etc., where examples of different formats are now reviewed in greater detail.

Multi-Parameter Co-Topo-Polymeric Indicator Compositions

Aspects of the invention include multi-parameter indicators that are formulated and based on co-topo-polymeric indicator compositions that incorporate a co-topo-polymeric indicator composition for temperature monitoring and at least one or more secondary indicators for determining the quality or state of a product being monitored. Secondary indicators in a multi-parameter indicator can include, but are not limited to, sensors that measure: food breakdown bi-products such as those from meat spoilage, pressure utilized in ultra-high pressure pasteurization equipment, high temperature indicators for measuring food cooking temperatures, pH for monitoring food processing conditions, gases emitted from a food product for monitoring food processing or storage states and the like.

Combination Co-Topo-Polymeric Compositions and Other Chromogenic Compounds:

Co-topo-polymeric compositions can be used alone, in direct contact and formulation with other chromic change agents, or in adjacent combinations with other chromic change agents. Other chromic change agents include, but are not limited to, other thermochromic, photochromic, mechanochromic, solvatochromic, chemochromic, biochromic, pressure chromic, pH indicators, environmental sensing compositions or the like. Importantly, the combination of the a co-topo-polymeric indicator composition can be utilized synergistically with one or more other chromic change agent to enable a multi-parameter indicating system.

Thermochromic dyes and colorants can be added to the composition formulation to serve as an indicating means to show that a particular composition has been temperature activated for optimal use. Temperature ranges for thermochromic transitions can be below freezing to above boiling depending on the intended use of the thermchromic composition application. Thermochromic dyes can find use in a variety of compositions and applications and formats. Thermochromic dyes can include but are not limited to compounds including: bis(2-amino-4-oxo-6-methylpyrimidinium)-tetrachlorocuprate(II); bis(2-amino-4-chloro-6-methylpyrimidinium) hexachlorod-icuprate(II); cobalt chloride; 3,5-dinitro salicylic acid; leuco dyes; spiropyrenes, bis(2-amino-4-oxo-6-methylpyrimidinium) tetrachlorocuprate(II) and bis(2-amino-4-chloro-6-methylpyrimidinium) hexachlorodicuprate(II), benzo- and naphthopyrans (Chromenes), poly(xylylviologen dibromide, di-beta-naphthospiropyran, Ferrocene-modified bis(spiropyridopyran), isomers of 1-isopropylidene-2-[1-(2-methyl-5-phenyl-3-thienyl)ethylidene]-succinic anhydride and the Photoproduct 7,7adihydro-4,7,7,7a-tetramethyl-2-phenylbenzo[b]thiophene-5,6-dicarboxylic anhydride, and the like.

Other thermochromic dyes of interest include leucodyes including color to colorless and color to color formulations, vinylphenylmethane-leucocynides and derivatives, fluoran dyes and derivatives, thermochromic pigments, micro and nano-pigments, molybdenum compounds, doped or undoped vanadium dioxide, indolinospirochromenes, melting waxes, encapsulated dyes, liquid crystalline materials, cholesteric liquid crystalline materials, spiropyrans, polybithiophenes, bipyridine materials, microencapsulated, mercury chloride dyes, tin complexes, combination thermochromic/photochromic materials, heat formable materials which change structure based on temperature, natural thermochromic materials such as pigments in beans, various thermochromic inks sold by Securink Corp. (Springfield, Va.), Matusui Corp., Liquid Crystal Research Crop., or any acceptable thermochromic materials with the capacity to report a temperature change or can be photo-stimulated and the like. The chromic change agent selected will depend on a number of factors including cost, material loading, color change desired, levels or color hue change, reversibility or irreversibility, stability, and the like.

Alternative thermochromic materials can be utilized including, but not limited to: light-induced metastable state in a thermochromic copper (II) complex (*Chem. Commun.,* 2002, (15), 1578-1579) under goes a color change from red to purple for a thermochromic complex, [Cu(dieten)2](BF4)2 (dieten=N,N-diethylethylenediamine); encapsulated pigmented materials from Omega Engineering Inc.; bis(2-amino-4-oxo-6-methyl-pyrimidinium) tetrachlorocuprate (II); bis(2-amino-4-chloro-6-methylpyrimidinium) hexachlorodicuprate(II); cobalt chloride; 3,5-dinitro salicylic acid; leuco dyes; spiropyrenes, bis(2-amino-4-oxo-6-methylpyrimidinium)-tetrachlorocuprate(II); bis(2-amino-4-chloro-6-methylpyrimidinium) hexachlorod-icuprate(II); cobalt chloride; 3,5-dinitro salicylic acid; leuco dyes; spiropyrenes, bis(2-amino-4-oxo-6-methylpyrimidinium) tetrachlorocuprate(II) and bis(2-amino-4-chloro-6-methylpyrimidinium) hexachlorodicuprate(II), benzo- and naphthopyrans (Chromenes), poly(xylylviologen dibromide, di-beta-naphthospiropyran, Ferrocene-modified bis(spiropyridopyran), isomers of 1-isopropylidene-2-[1-(2-methyl-5-phenyl-3-thienyl)ethylidene]-succinic anhydride and the Photoproduct 7,7adihydro-4,7,7,7a-tetramethyl-2-phenylbenzo[b]thiophene-5,6-dicarboxylic anhydride, and the like. Encapsulated leuco dyes are of interest since they can be easily processed in a variety of formats into a plastic or putty matrix. Liquid crystal materials can be conveniently applied as paints or inks to surfaces of color/shape/memory composites.

Thermochromic color to colorless options can include by way of example, but not by limitation: yellow to colorless, orange to color less, red to colorless, pink to colorless, magenta to colorless, purple to colorless, blue to colorless, turquoise to colorless, green to colorless, brown to colorless, black to colorless. Color to color options include but are not limited to: orange to yellow, orange to pink, orange to very light green, orange to peach; red to yellow, red to orange, red to pink, red to light green, red to peach; magenta to yellow, magenta to orange, magenta to pink, magenta to light green, magenta to light blue; purple to red, purple to pink, purple to blue; blue to pink; blue to light green, dark blue to light yellow, dark blue to light green, dark blue to light blue; turquoise to light green, turquoise to light blue, turquoise to light yellow, turquoise to light peach, turquoise to light pink; green to yellow, dark green to orange, dark green to light green, dark green to light pink; brown and black to a variety of assorted colors, and the like. Colors can be deeply enriched using fluorescent and glow-in-the-dark or photoluminescent pigments as well as related color additives.

Reversible and irreversible versions of this optional color change agent can be employed, depending on the desired embodiment of interest. Reversible agents can be employed where it is desirable to have a multi-use effect or reuse the color change effect. For example, products with continued and repeated use value will find utility of a reversible color change component comprising the final embodiment. In this case it would be desirable to utilize a reversible thermochromic or luminescent material which can be repeated during usage. In another example, it may be desirable to record a single color change permanently. In this case, it would be desirable to utilize a thermochromically irreversible material which changes from one color to another giving rise to a permanent change and indicating that the composition should be discarded after use.

Luminescent or fluorescent pigments can be used in conjunction with co-topo-polymeric compositions. Non-visible spectrum fluorescent dyes can be obscured by one color of a diacetylenic composition or other thermochromic dye such that when a temperature triggering event occurs, the fluorescent signal becomes visible when utilizing the corresponding wavelength to reveal the fluorescent dye composition.

Optical Pattern and/or Message Development:

Optical patterns can be developed under triggering conditions using optical color change dye systems in combination with modeled substrate surfaces. An image can be generated by applying a pressure indicating film over a substrate layer that has been pre-surface textured or patterned. As temperatures are induced the dye layer initially comes in contact with the close proximity regions or features of the patterned substrate surface. An initial color change will occur in the dye layer that emulates the upper surfaces of the substrate. As temperatures continue to increase, the dye layer may be forced in contact with lower regions of the substrate surface texture. Images or patterns can appear differentially as a result of the final temperature induced between the temperature indicating dye layer and the patterned or textured substrate. Partial images can be made to occur at lower temperatures. More complete or developed images or messages can be made to appear at medium pressures. Fully developed images or completed messages can be made to appear at final desired induced temperature.

Passive and Active RFID Temperature Integrating Devices:

In certain embodiments, energies generated in RFID circuits can be utilized as a stimuli to selectively and locally induce an optical change in color change compositions. Highly sensitive and responsive compositions can be printed selectively and adjoined with a passive or active RFID devices such that radio wave stimuli sent to the RFID device can be utilized to induce a color change dependent response. The response can be triggered in the RFID circuit for the purpose of adding a visual indication means to the RFID device which otherwise, would not only be visible during and RFID tag usage event.

Encapsulation:

Co-topo-polymeric indicator compositions and/or components of the precursor compositions can be co-encapsulated with existing chromic change agents, mixed with micro-encapsulated agents, separately micro-encapsulated or be utilized in combination with a second chromic change composition. How a co-topo-polymeric composition is utilized alone or in combination with a second chromic change composition will depend on the application of interest, operating conditions, elements to be measured and the like.

A co-topo-polymeric composition can be prepared using an encapsulating coating that responds to particular pressures of interest by adjusting the coating thickness and coating type. Acid/base color change systems, donor acceptor color change composition systems, activator/dye systems, or charge transfer color change composition systems may be encapsulated using standard leuco dye encapsulating processes. The hardness, strength, integrity and pressure fracture properties of the encapsulation compositions may be selected to match a particular pressure level of interest. Encapsulation coatings and processes may be further adjusted as to not interfere with the chemical color change properties of the color change system. Encapsulated dye systems can be further processed into ink or coating formulations including a liquid carrier medium that is compatible with the suspension and stabilization of an encapsulated dye, a binder for adhering the dye system to a substrate, and any necessary stabilizing components needed to mitigate any unwanted dye migration and unwanted color development. Emulsifier and surfactants can be further added to improve coating and flow characteristics during application of the dye ink to a substrate layer. Processed coating solutions can be adhered directly to a substrate, film, surface, bottom substrate layer or other convenient surface intended as part of a finished pressure indicator.

Chromic change/indicating dyes can be added in from 0.001% by weight to 80% by weight, such as from 0.01% to 50% by weight, including from 0.1% to 25%, e.g., from 0.5% to 5%.

Common Colorants and Pigments:

Fluorescent dyes and pigments can find use in various product applications and mediums and formats to improve the coloration of the initial product as well as acting to create a strong contrast in the composition matrix indicating that a contaminating species has been transferred into the matrix. Fluorescent dye compounds can include, but are not limited to: fluorescein, fluoresceine, resourcinolphthalein, rhodamine, imidazolium cations, pyridoimidazolium cations, dinitrophenyl, tetramethylrhodamine and the like. A wide range of fluorescent dyes that can be activated at various wavelengths and emit light at lower wavelengths can be purchased from Dayglo Inc., Swada Chemical, Sigma-Aldrich (Saint Louis, Mo.) or Molecular Probes (Eugene, Oreg.).

Homogeneous Oil Droplet and Micro-Particulate Dispersions:

Uniform and homogeneously dispersed micro, nano, macro colloidal units can be utilized to assist in more homogeneous and tighter distribution of temperature transition behaviors of co-topo-polymeric indicator compositions compared with compositions that have a range of distribution of micro-crystalline sizes. In general, it is anticipated that uniform crystalline micro and nano-crystalline sizes provide for a more stochastic conformational changes at specifically selected and/or desired temperature triggering points.

Dispersion sizes of colloidal oil droplets of co-topo-polymeric compositions can range in size from 1000 microns to 0.001 microns, such as from 500 microns to 0.01 microns, including from 250 microns to 0.5 microns, e.g., from 100 microns to 1.0 microns.

Dispersion methods can include, but are not limited to simple mixing, vortex mixing, sheer mixing, sonication, ultra-sonication, blade mixing, shaking, orbital shaking, stirring, vibratory mixing and the like. Mixing can be accomplished in durations that lead to consistent homogeneous dispersions or mixed heterogeneous solutions. Mixing times may range from 100 hours to 0.1 second, such as from 10 hours to 1 second, including from 10 hours to 10 seconds, e.g., from 1 hour to 1 minute. The exact energy and time delivered to the composition will depend not only on the composition, but on the final desired species size and homogeneity desired.

Dispersion Compositions and Printing Vehicles and Additives:

Dispersive and printing vehicles and additives can comprise constituents that conveniently assist in generating highly uniform and dispersed co-topo-polymeric compositions. Dispersion compositions and printing vehicles of interest are formulated to have the properties of adequately dispersing the composition of interest, providing a convenient and acceptable printing and binding vehicle to a substrate of interest, and preserving the binding, crystallization, and polymerization characteristics of interest. Likewise, a dispersive/printing vehicle of interest provide expediency of crystallization.

Nucleators for Crystal Homogeneity and Crystallization Control

Nano-, micro-, or macro-nucleation additives may be present in the precursor compositions. Such additives can be based on substrate-monomer interaction, monomer-nucleator interaction, a combination of interactions between both the substrate and nucleator. Nucleating compositions can include, but are not limited to: micro-particulates, silicon oxides, lake dyes, dye pigments, ground inorganic materials, salts, minerals, diatomaceous earth, oxides, gels, chromatographic resins, resins, starburst dendrimers, carbon, nanotubes, nano particles, cellulosic particles, glass, fine metal particles, structured surfaces, structured substrates, ink pigments, vapor deposited compositions, polymeric resins, and the like.

Nucleating agents can be added at percentages that promote a desired nucleation/crystallization response of interest. Nucleating agents can be added and can be effective from 0.0001% by weight to a soluble monomer composition to greater than 90% by weight, such as from between 0.001% up to 80% by weight, including from between 0.01% up to 70% by weight, e.g., from between 0.1% and up to 50% by weight, where in some instances agent will be present in amounts between 1% and 25% by weight.

Nucleator sizes can be of use for controlling and facilitating crystallization processes. Nucleator sizes can range from 1000 microns to 0.001 microns, such as from 500 microns to 0.01 microns, including from 250 microns to 0.5 microns, e.g., from 100 microns to 1.0 microns.

Various nucleation methods, sequences, composition formulation procedures and the like can be employed for facilitating and formulating utilizing a nucleating agent. Nucleating agents can be added or admixed during various stages of ink preparation. Nucleating agents can be added as an initial component where by co-topo precursor compositions and printing vehicle components can be added subsequently. Nucleating agents can be added to pre-mixed ratios of monomeric materials of co-topo-polymeric precursor compositions for co-topo polymeric indicator compositions. Alternatively, nucleating agents can be added post formation of a co-topo composition that is intended as a fully functional printing vehicle whereby on the nucleating agent must be further added. Likewise, the nucleating agent can be pre-printed on an intended printing substrate such that the nucleating agent is part of a printable layer that the co-topo-polymeric composition is intended to be subsequently printed on. Intimate contact between the nucleating agent and the co-topo polymeric precursor composition should be facilitated in any of the above examples.

Combination Homogeneous Dispersion-Nucleating Agents

A combination of utilizing homogeneous dispersions and nucleating agents have a combined synergistic advantage of generating a narrow distribution of temperature transitions for a given topo-polymeric indicator composition. Likewise, one or more nucleating agents can be employed with a particular co-topo-polymeric indicator composition.

Anti-Oxidants/Preservatives

Various antidoxidant and/or preservatives may be included in compositions of the invention. Examples of compounds having anti-oxidant and/or preservative activity include, but are not limited to: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Methods of Making Co-Topo-Polymeric Indicator Compositions

As summarized above, in preparing an indicator composition from a precursor composition, e.g., as described above, the monomers and other components of the precursor composition may be admixed in a dissolved state and then applied to an item of interest, e.g., an item to be monitored or a substrate.

As indicated above, indicator compositions of the invention may be present on a substrate. Indicating substrate compositions include but are not limited to paper, plastic, hard surfaces, soft surfaces, stiff or rigid surfaces, compliant surfaces, printed surfaces, printable surfaces, transparent surfaces, semi-transparent surfaces, opaque surfaces, non-transparent surfaces, porous and non-porous surfaces, and the like. A substrate composition can be comprised of thick or thin materials, e.g., ranging in thickness from 1 nanometer to 100 centimeters, such as from 10 nanometers to 10 centimeters, including from 1 micron to 1 centimeter, such as from 10 microns to 5 millimeters, e.g., 0.1 millimeters and 1.0 millimeters. In some instances, the indicator composition is laminated onto a surface of the substrate, such as a plastic substrate. In certain instances, chemically active substrates are employed for compositions such that the composition's temperature monitoring capabilities can be further modified by interaction with a chemically active component embedded in the substrate.

Following application of the precursor composition, e.g., directly to the item of interest or to a substrate (such as described above), the applied composition is allowed to set, e.g., where the monomeric components of the precursor composition are allowed to co-crystallize. Optimal crystallization conditions for monomers and mixed monomer systems of co-topo-polymeric precursor compositions can dictate and play an important role in determining the crystal quality, polymerization characteristics, and resultant threshold temperature transition of a co-topo-polymeric composition. Annealing processes can be utilized to ensure optimal control over crystal quality. Of particular interest are oil-based compositions of co-topo-polymeric precursor monomer materials. Room temperature oils may undergo various phase transitions from a completely fluid-liquid oil phase to a smectic crystal to an order crystalline phase.

Oil-base diacetylenic monomers exhibit properties similar to liquid crystals used through out technology based products. Liquid crystals are partly ordered materials, somewhere between their solid and liquid phases. Their molecules are often shaped like rods or plates or some other forms that encourage them to align collectively along a certain direction. The order of liquid crystals can be manipulated with mechanical, magnetic or electric forces. Finally, liquid crystals are temperature sensitive since they turn into solid if it is too cold, and into liquid if it is too hot.

At some point following application of the precursor composition to the item of interest or substrate, the precursor composition is activated into the indicator composition via polymerization. In some instances, the precursor composition is polymerized by subjecting the composition to polymerization conditions. As indicated above, precursor compositions are subjected to polymerization conditions in order to produce the desired indicator compositions. Polymerization conditions of interest include, but are not limited to: ultra violet light, gamma radiation, cobalt-60 radiation and electron beam radiation, etc. The precursor compositions may be subjected to polymerization conditions after application to a substrate, e.g., as described in greater detail below.

In some instances, precursor compositions may be configured to auto-polymerize for self-activation. In such instances, the precursor compositions may immediately auto-polymerize, or polymerize after some time delay, including the time frames described elsewhere in connection with time delay applications.

Mixed systems may or may not require that each mixed analog in a composition be independently polymerizable, so long as the resulting combination is polymerizeable.

Polymerization may occur immediately following application or at some point after application. In some instances, the polymerization of a precursor composition may itself be employed in a given application, i.e., to determine whether an item of interest was subjected to polymerization conditions, which may or may not have been desirable depending on the nature of the item of interest.

In certain instances, methods of making indicator compositions of the invention which may be used to readily determine whether a product has been exposed to a condition (e.g., temperature) detrimental to the product may include the following steps: positioning the product in proximity to a indicator precursor composition; bringing positioned product to a non-critical exposure level away from the certain value of the condition; and polymerizing the precursor composition when the product is in the non-critical exposure level. Embodiments of such methods may further include selecting said composition to match a desired critical temperature.

Methods of interest may further include assigning a maximum value that the temperature the product should be exposed to at each stage throughout a supply chain; and monitoring the printed material for exposure to the assigned values at each said stage.

Also of interest are methods for displaying whether a product in a home has been exposed to a temperature condition detrimental to said product. Such methods may include attaching a printed material to the product, where the printed material includes an indicator precursor composition of the invention and polymerizing the precursor composition after the printed material has been attached to the product and after a temperature of the printed material has been placed below the detrimental temperature condition.

Temperature Adjustment Formats:

Modulation, adjustment, tuning, increasing or decreasing, augmenting, phase shifting, elevating or descending, altering phase diagrams or the like of temperature of co-topo-polymeric compositions can be accomplished by mixing ratios of 2 or more analogs as disclosed herein. Various points in the process of producing a temperature indicating composition, marking, label, or device can be utilized for adding an analog or combining 2 or more analogs such that a final temperature setting is achieved.

By way of example, but not limitation, forms of co-topo-polymerizable monomers (i.e. precursor compositions) can be pre-mixed prior to further processing and at the initial stage of formulation from in their neat or pure form from 0.001% of a first component to 99.999% of a second component, such as in the range of 0.01 of a first component to 99.99% of a second component, including in the range from 0.1% of a first component to 99.9% of a second component, e.g., in the range from 1% of a first component to 99% of a second component. The exact ratio of each component will be selected based on the desired temperature setting and characteristics of the intended product application for the composition. Likewise, ratios of two or more monomers can be established using standard approaches for determining phase diagrams and temperature threshold curves. Complex ratios of 3 or more individual monomers can further be achieved by the same approach.

Subsequent to pre-mixing monomer ratios, the mixed compositions, providing a pre-determined temperature threshold, can be added to a printing vehicle or become an initial component of a formulation that is intended to become a final printing vehicle. Likewise, in certain cases, the pre-mixed composition can be used directly on a substrate and utilized without further alteration with the exception of applying the mixed composition to the substrate.

In a second example, pre-determined ratios of selected monomers that are intended to comprise a final composition can be added at a different stages of a formulation or production process. A first component can be added in the process of ink/vehicle formulation where as a second component can be added at a later stage in the formulation, to a substrate that has been pre-printed with a first component, or at any other convenient point in the process of making a temperature indicating device. Final processing is performed in a manner sufficient to ensure that the intended ratios of monomers admix or come in contact with one another to provide for the co-mixing effect.

Mixed co-topo-polymeric compositions provide for on-demand temperature adjustments whereby in initially printed and exposed single component can be post-modified by subsequently printing a second component such that the second component comes into direct contact with part or all of the printed area of the first component. The volumes and concentrations of each component are pre-determined such the final ratios represent the ratios required for a pre-selected temperature setting based on predetermined phase diagram tests.

Patterns or gradients can be generated in either the first printed component or the second printed component such that an intended temperature gradient or patterned graphic results during the temperature triggering process. For example, a simple strip can comprise 100% of one component at one end and 100% of a second component at the other end. A gradient of composition ratios can be created from on to another either in a continuous manner or in a step function. In either case, the gradient from one end shall represent an initial low temperature threshold where as the gradient at the other end will represent a final high temperature threshold. Thermometer strips can be prepared and printed such that a color change will occur geometrically along the strip as exposure temperatures are increased from the initial triggering temperature to the final temperature.

FIG. 1 is a graph showing color change temperatures plotted against mixtures with different indicator compositions fabricated from different precursor concentrations of one or more miscible monomers. The vertical axis represents the temperature. The horizontal axis represents the concentration of different mixtures of monomers $A_n$ and $B_n$ in the relevant precursor composition. The curve represents the temperature at which a particular indicator composition changes color. The concentration of $A_n$ decreases from left to right while the concentration of $B_n$ increases from left to right. For example, monomers $A_1$ and $B_1$ are mixed together to form a precursor and ultimately indicator $A_1B_1$; $A_2$ and $B_2$ are mixed together to form a precursor and ultimately indicator $A_2B_2$; and $A_3$ and $B_3$ are mixed together to form a precursor and ultimately indicator $A_3B_3$. At the left vertical axis, the concentration of the monomers $A_1$, $A_2$ and $A_3$ is 100% and the concentration of monomers $B_1$, $B_2$ and $B_3$ is 0%. At the right vertical axis, the concentration of monomers $A_1$, $A_2$ and $A_3$ is 0% and the concentration of monomers $B_1$, $B_2$ and $B_3$ is 100%. Curves 101, 102 and 103 represent temperature-concentration curves for indicators $A_1B_1$, $A_2B_2$ and $A_3B_3$, respectively.

From the graph 100, it can be concluded that it requires a higher temperature to effect a color change in any indicator composition of mixture $A_1B_1$ as compared with the compositions of $A_2B_2$ and $A_3B_3$. As seen at the vertical axis, $A_2$ and $A_3$ change color at the same temperature. However, possibly because of $A_2$'s and $A_3$'s different reaction to increased temperature or the effect of $B_2$ and $B_3$ on $A_2$ and $A_3$ respectively, the mixtures $A_2B_2$ and $A_3B_3$ exhibit different temperature-concentration curves.

Figure 2:
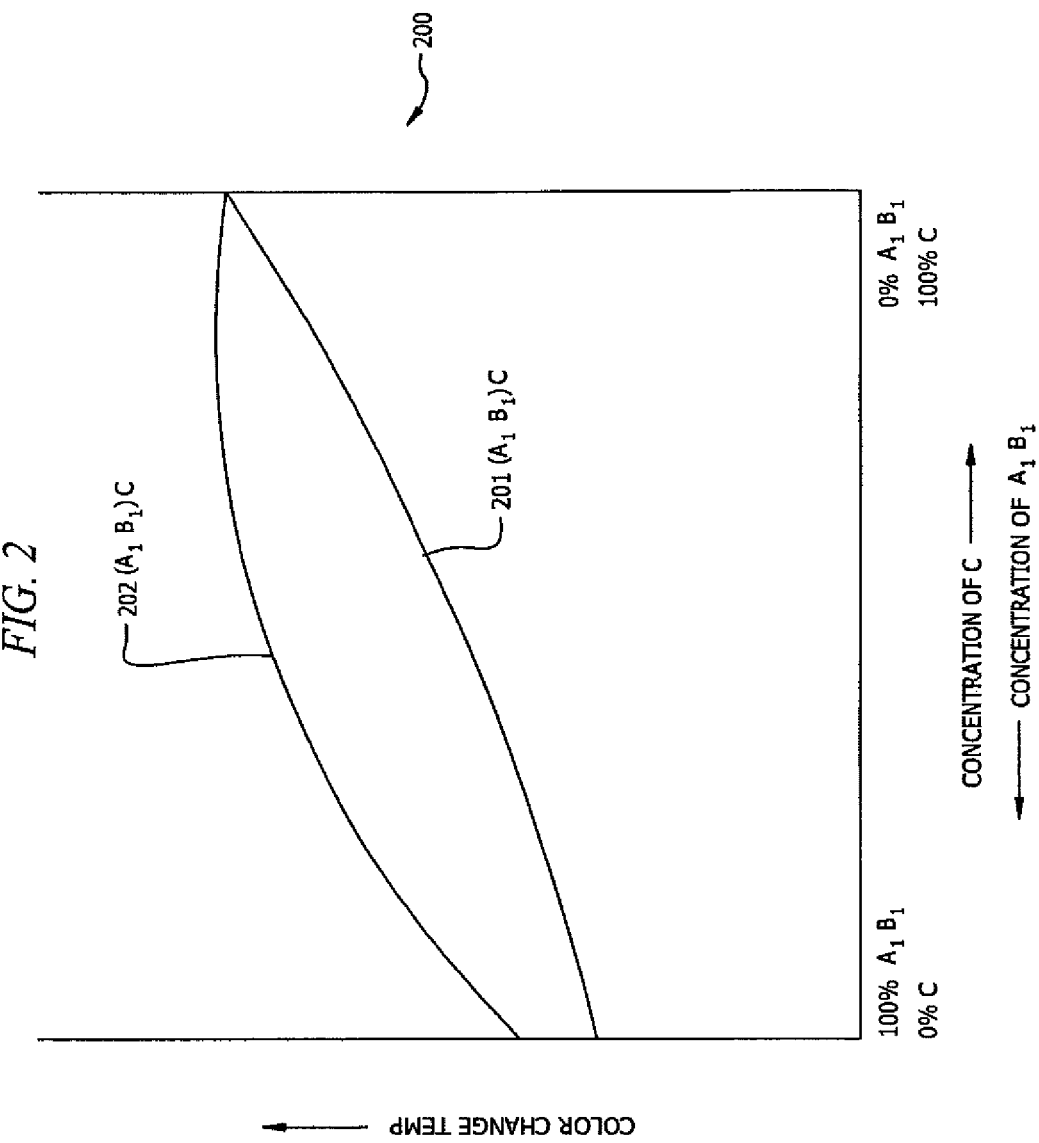
FIG. 2 is a graph showing color change temperature plotted against different co-topo-polymeric indicator compositions that are made from different precursor compositions having differing concentrations of three different miscible monomers.

FIG. 2 depicts graph 200 showing how a mixture $A_1B_1$ as illustrated in FIG. 1 can be mixed with another monomer to get a mixture of three monomers which exhibits a different temperature composition curve from each of its component monomers or sub-combination of monomers. In the first example, curve 201 represents the temperature-composition curve of a mixture of $A_1B_1$ mixed with monomer C to form mixture $(A_1B_1)C$ wherein the $A_1B_1$ mixture remains proportionally stable in relationship to each other at 50% $A_1$ and 50% $B_1$. Curve 202 on the other hand, while containing a mixture of $A_1B_1$ and C, the $A_1B_1$ mixture contains 25% $A_1$ and 75% $B_1$. The temperature color change curve is different in 202 from 201 because the makeup of the $A_1B_1$ compositions are different. From FIGS. 1 and 2 therefore, it can be seen that to get a desired temperature-concentration curve one only needs to find the appropriate combination of monomers in a precursor composition. It should be noted that additives, pigments, dyes, non-polymerizable monomers, polymers, antioxidants, stabilizers, polymerization initiators, polymerization control agents, etc., may be added to miscible monomers $A_n$ and $B_n$ or mixtures thereof to perform various functions without having deleterious effect on the temperature-concentration curve. Some additives are inert and do not affect the color change properties of the indicator compositions prepared from monomers $A_n$ or $B_n$ or mixtures thereof. One additive that may be used to affect the color change property, however, is an additive that delays the color change in response to increased temperature such that the indicator requires exposure to a particular temperature for a minimum predetermined amount of time before the color change occurs.

Printing

Co-topo-polymeric compositions can be readily printed using a wide range of conventional and innovative printing mechanisms. Printing can be accomplished using high-speed methods such as flexographic printing, rotogravier, off-set printing and the like. Printing can also be accomplished using medium speed processes such as screen printing, rotary screen printing, and fluid application. Printing can be accomplished using ink jet printing, drop on demand printing, continuous ink jet printing, valve-jet printing, spray coating, dropping methods, flood coating methods, dip coating methods, metering methods and other fluid application systems, film transfer methods, dye sublimation processes, and the like. The exact printing method utilized will depend on the type of printing required, formulations utilized, device configurations, volume requirements and the like.

Using any mixture of monomers $A_n$ and $B_n \ldots N_n$, an indicator compositions, such as a printable indicator composition, may be made by suitably dispersing monomers $A_n$ and $B_n \ldots N_n$, in a water based rotogravure vehicle such as ColorTell Thermochromic Water Based Vehicle available from Clark R&D Ltd. The invention, however, is not limited to this water based vehicle. The water based vehicle acts as a carrier for the monomers so the monomers can be put on a substrate, for example paper. It could be a smooth coating, or it could be a unique character like a letter or a number. In one embodiment of the invention, the printable ink is capable of working on a printing press at high speeds. The carrier also serves the purpose of keeping the monomers in place, that is, where it was initially placed on a substrate. An example of the composition of a printable ink is: 5-50% monomer dispersed in 95-50% water based rotogravure vehicle (such as ColorTell Thermochromic Water Based Vehicle).

Compositions disclosed here within have been tested and analyzed for activities and function in a wide range of printing vehicles including water-based, solvent based, ultra-violet light cured, single component curable resins, dual component epoxy printing resins, sublimation resins, oil base vehicles, fast drying and slow drying vehicles, pigmented and non pigmented resins, clear and opaque vehicles, and a wide range of conventional and non conventional printing resins and the like. The exact printing vehicle utilized will depend on the type of printing required, formulations utilized, device configurations, volume requirements and the like.

Where desired, various approaches may be employed for mitigation of diffusion of deposited compositions on various substrate surfaces. For example, post coating/diffusion inhibitors of sensor zones for sealing oil-based monomers and polymers may be employed. Alternative or in addition, non-diffusive substrates may be employed. Alternatively, diffusion may be exploited and controlled in order to obtain a desired indicator composition.

Figure 3A:
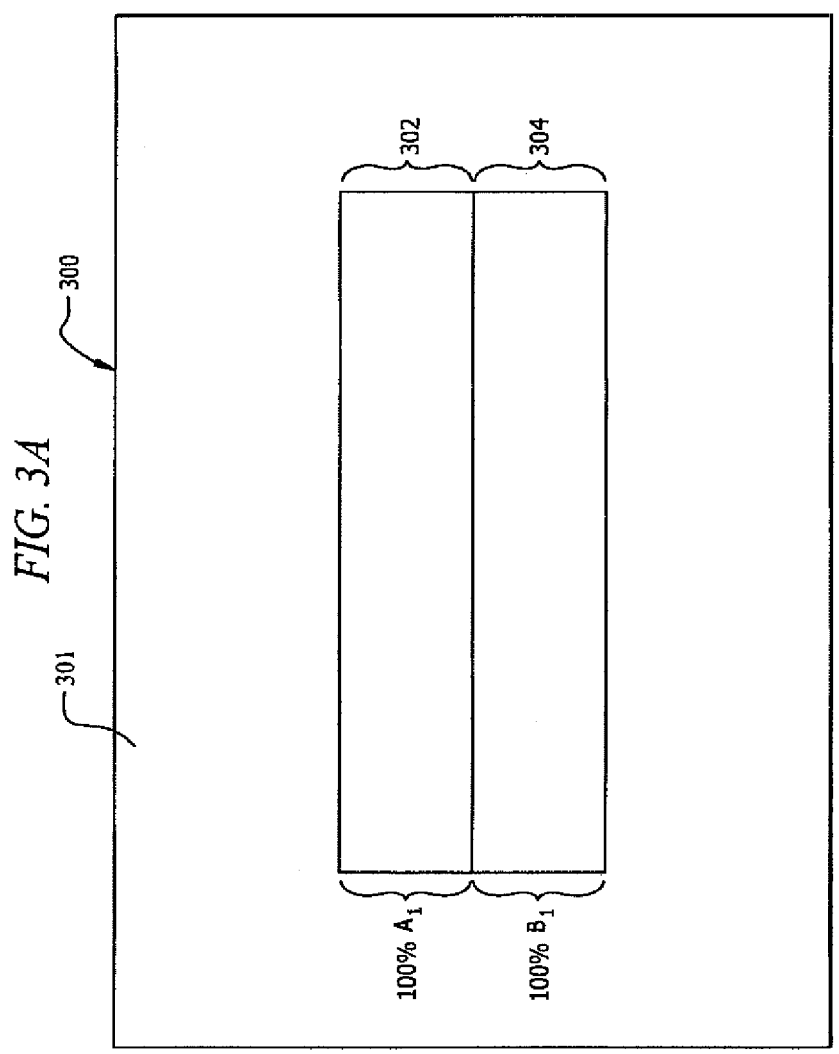

FIGS. 3A-3C show the printing of inks with single monomers to create mixture of monomers on a substrate, and thereby product a precursor composition on a substrate. Once a monomer has been dispersed in a suitable vehicle to form a printable ink, the printable ink may be used for printing on various substrates including but not limited to paper, film, foil, textile, fabric, plastic, parchment.

FIG. 3A shows a printed substrate 300. On substrate 301, two strips of printable ink 302 and 304 are laid down alongside each other. Printable ink strip 302 contains 100% $A_1$ while printable ink strip 304 contains 100% $B_1$. FIG. 3A shows printed substrate 300 immediately after printable ink strips 302 and 304 are applied to substrate 301.

FIG. 3B shows printed substrate 300 after the passage of a sufficient period of time after applying ink strips 302 and 304, where there is diffusion of printable ink 302 into portions of substrate 301 previously occupied by printable ink 304 only, and vice versa. In effect, a mixture of $A_1B_1$ is created in the areas of the strip where diffusion has occurred-diffused area 305.

FIG. 3C shows printed substrate 300 after an extended period of time to allow complete diffusion of printable ink 302 and 304 into each other. When printable ink strips 302 and 304 completely diffuse into each other, diffused area 305, containing a mixture $A_1B_1$, now occupies all the area of the substrate previously occupied by printable strips 302 and 304. Assuming complete and uniform diffusion, area 305 would contain uniform concentration of monomers $A_1$ and $B_1$. If area 305 contains 50% $A_1$ and 50% $B_1$ area 305 would have a single color change temperature represented by point 104 on temperature concentration curve 101 as depicted in FIG. 1. Thus, area 305 would irreversibly change color on reaching temperature $T_2$ shown in FIG. 1.

Figure 4A:
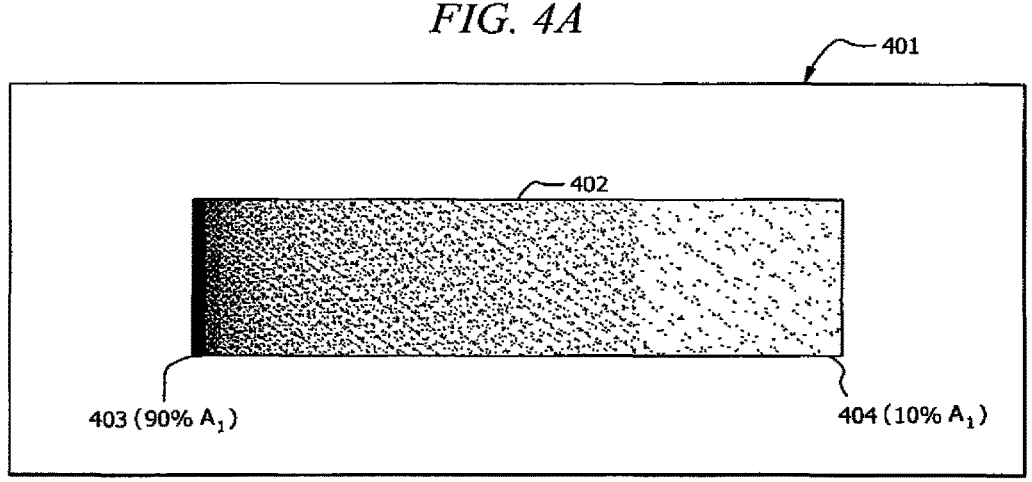
Figure 4B:
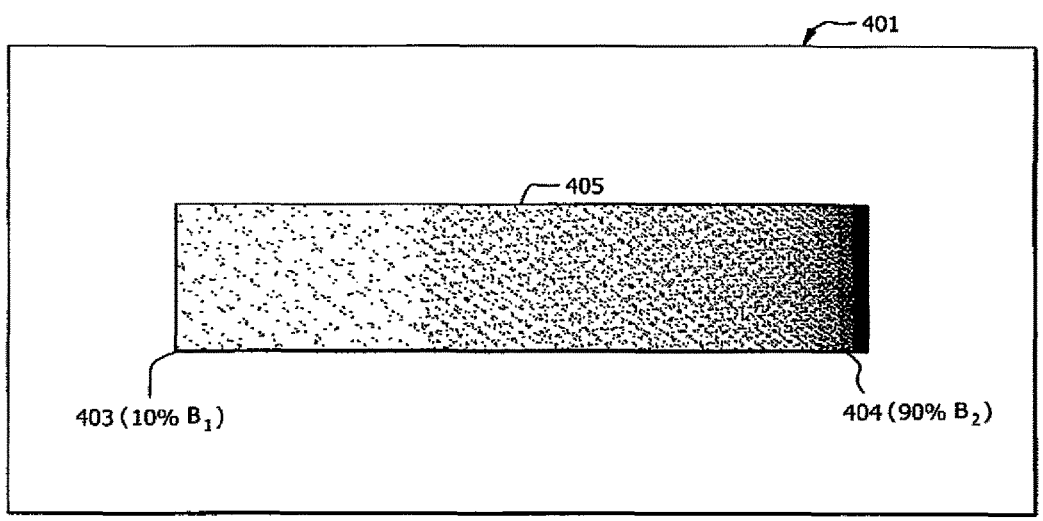

FIGS. 4A-C shows how irreversible thermochromic inks are applied to a substrate to create a strip of ink with portions that irreversibly change color at different temperatures. FIG. 4A shows printed substrate 401 with ink strip 402 containing monomer $A_1$ printed on substrate 401. The ink strip 402 contains varying proportions of $A_1$ along the strip. At point 403, ink strip 402 has 90% $A_1$. This concentration gradually decreases along ink strip 402 towards point 404. At point 404 the strip has a concentration of 10% $A_1$. Before the ink on printed substrate 401 dries, ink strip 405 is printed on top of printable ink strip 402.

FIG. 4B shows substrate 401 with printable ink strip 405 that is placed on printable ink strip 402, before printable ink strip 402 dries. Points 403 and 404 represent corresponding points on printable ink strips 402 and 405 because, in the example, printable ink strips 402 and 405 are the same shape and size. However, point 403 (on printable ink strip 405), has a concentration of 10% monomer $B_1$. The concentration of monomer $B_1$ consistently increases along strip 405 towards point 404. At point 404, the concentration of monomer $B_1$ is 90%.

FIG. 4C is an exaggerated elevation view 406 of printable ink strip 405 on top of printable ink strip 402 immediately after printable ink 405 is placed top of printable ink strip 402 and a corresponding graph 407. With the passage of time, however, ink strips 402 and 405 will diffuse into each other. Line 408 of graph 407 illustrates the temperature gradient that exists along the combination of ink strips 402 and 405 on substrate 401 as a result of the varying concentrations of monomers $A_1$ and $B_1$ in the mixture $A_1B_1$ created by printing printable ink strips 402 and 405 on substrate 401 and the diffusion that occurs to create the mixture $A_1B_1$. In the printing process the printable inks are printed in screens, effectively dots. In the printing process, the varying proportions of A along the strip is created by the image on the printing plate in the case of Flexographic or Offset printing; the creation of the cell pattern on a rotogravure cylinder; the dot pattern (or image screen) on a silk screen fabric; or by the density of an inkjet dot pattern along the strip.

FIGS. 5A-5B shows how a printed product with multiple temperature-concentration curves may be made. FIG. 5A shows the first step in the process to make a printed strip with multiple temperature-concentration curves. Multiple spaced inks of different compositions $A_1B_1$, $A_2B_2$ and $A_3B_3$ are printed onto a common ink C. Ink C is on substrate 501. C may also have its own unique and different temperature-concentration curve from compositions $A_1B_1$, $A_2B_2$ and $A_3B_3$.

FIG. 5B shows the printed strip with $A_1B_1$, $A_2B_2$ and $A_3B_3$ compositions and ink C after diffusion occurs. During diffusion, $A_1B_1$ diffuses in a certain portion of C as does $A_2B_2$ and $A_3B_3$. Thus, to create a multi-temperature-concentration ink along the substrate either C or $A_1B_1$, $A_2B_2$ and $A_3B_3$ must be printed on the substrate at varying concentrations. The resulting $(A_1B_1)C$, $(A_2B_2)C$ and $(A_3B_3)C$ combinations result in a multi-temperature-concentration gradient because each combination would have a temperature-concentration curve as shown in graphs 502-1, 502-2 and 502-3 showing curves 502-a, 502-b and 502-c, respectively.

FIG. 6A-E illustrate the color changes that occur for irreversible indicator composition printed on substrate 401 as shown in FIGS. 4A-C. After complete diffusion occurs in printed coating combination of ink strips 402 and 405 (containing mixture $A_1B_1$), the coating is allowed to dry. The dried coating 402 and 405 is cooled below the respective minimum color change temperature along the gradient and then polymerized. In this polymerized and crystallized state, the strip of coating may be blue. As long as the environmental temperature of the coatings remains below the lowest minimum color change temperature, the blue crystallized state is stable. As the temperature is raised, each portion of the coating, in turn, will change from blue to, for example, pink according to their respective temperature-concentration curve. Thus, those portions of each coating corresponding to the lowest color change temperature will turn pink first and those with the highest color change temperature will turn pink last.

Figure 6A:
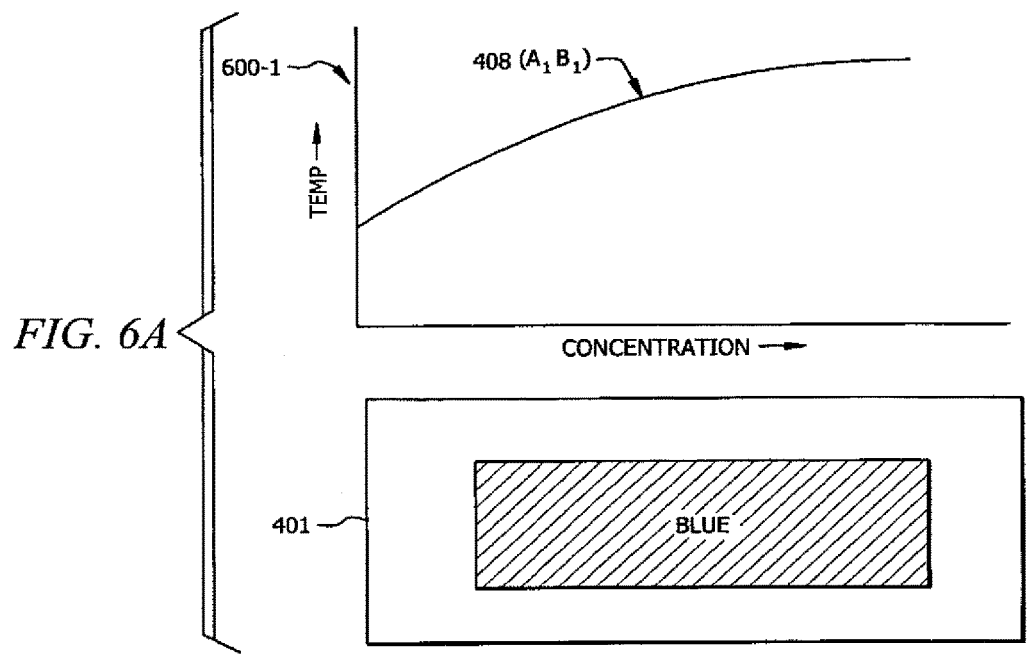
FIGS. 6A-E illustrate a printed product, with a color change temperature curve, that changes color with increasing temperature.
Figure 6B:
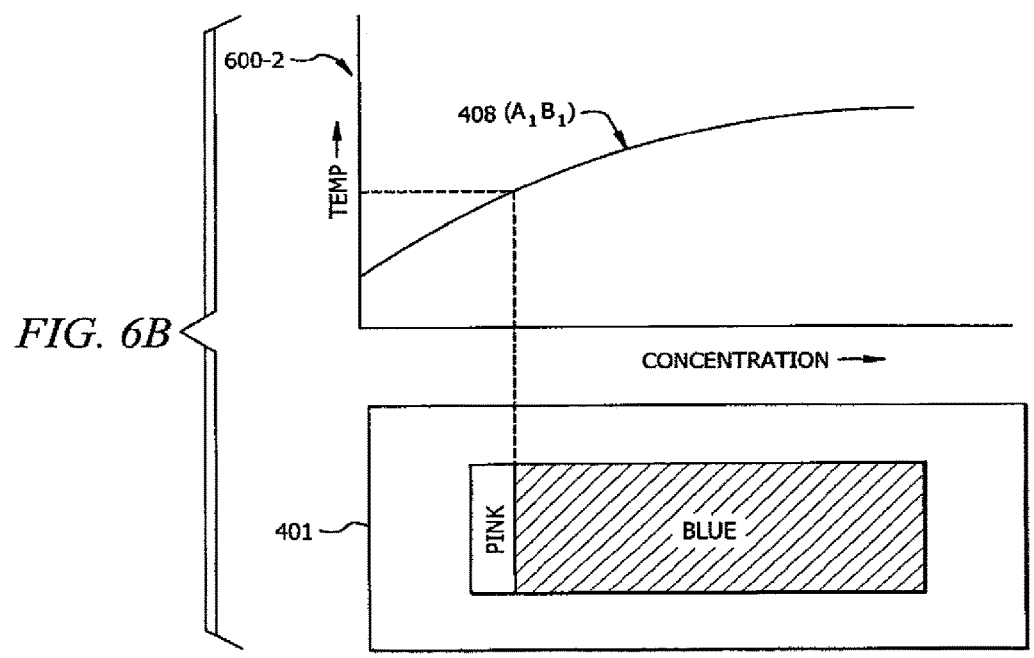
Figure 6C:
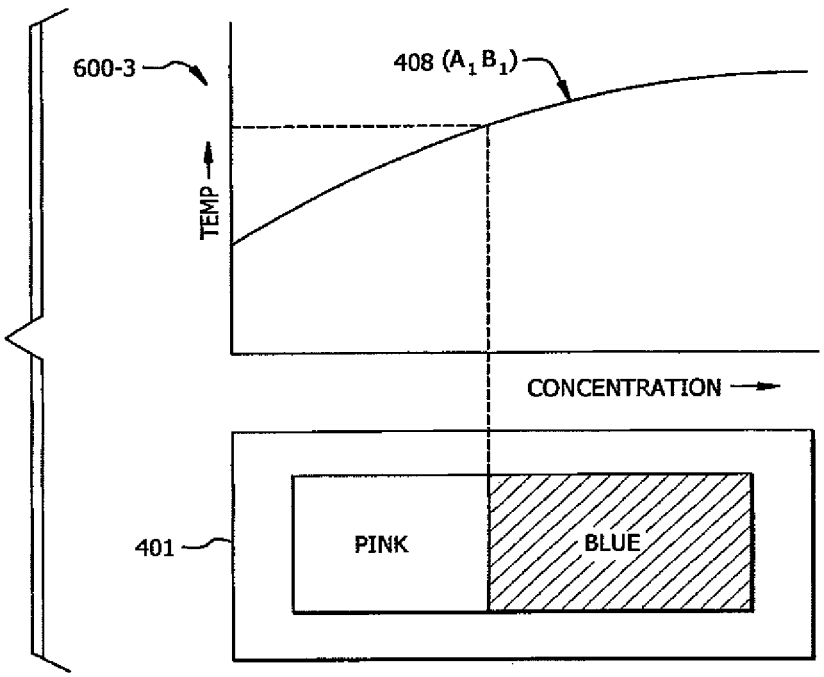

For example, FIGS. 6A-E shows that coating $A_1B_1$, as illustrated in FIG. 4C, may be a blue crystallized coating after cooling below its minimum color change temperature and polymerization. FIGS. 6A-E also show that $A_1B_1$ will progressively change color as the minimum color change temperature is surpassed and the temperature continues to increase. In FIG. 6A all of the coating is blue because the minimum color change temperature has not been reached. As the temperature is increased to just above the minimum color change temperature the first color change from blue to pink occurs in FIG. 6B. As the temperature is increased to a temperature $T_1$ (FIG. 1) where 35% of the $A_1B_1$ coating has a composition that changes color at a temperature equal to or less than the increased temperature, then 35% of the coating will be pink and the remaining 65% will remain blue as shown in FIG. 6C.

Figure 6D:
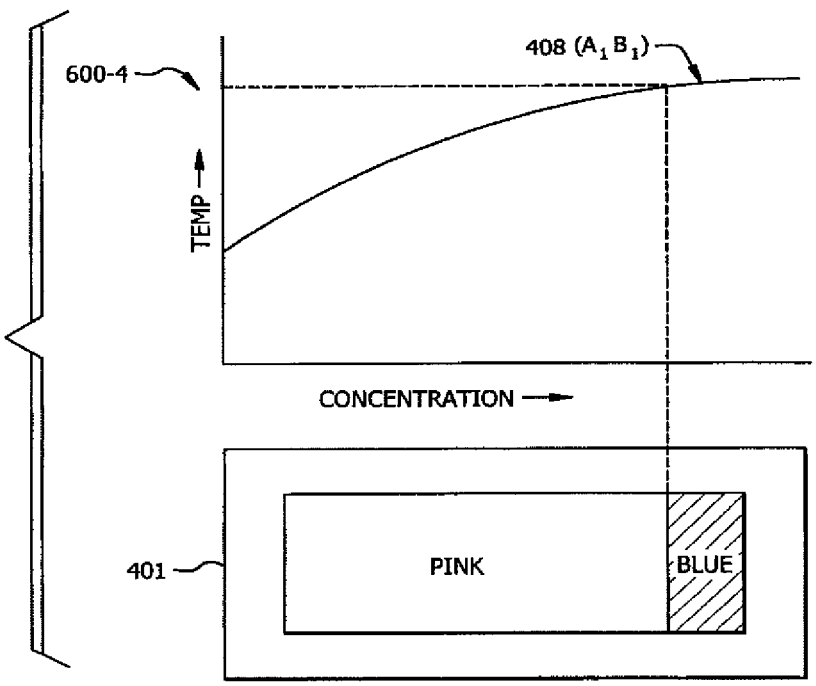
Figure 6E:
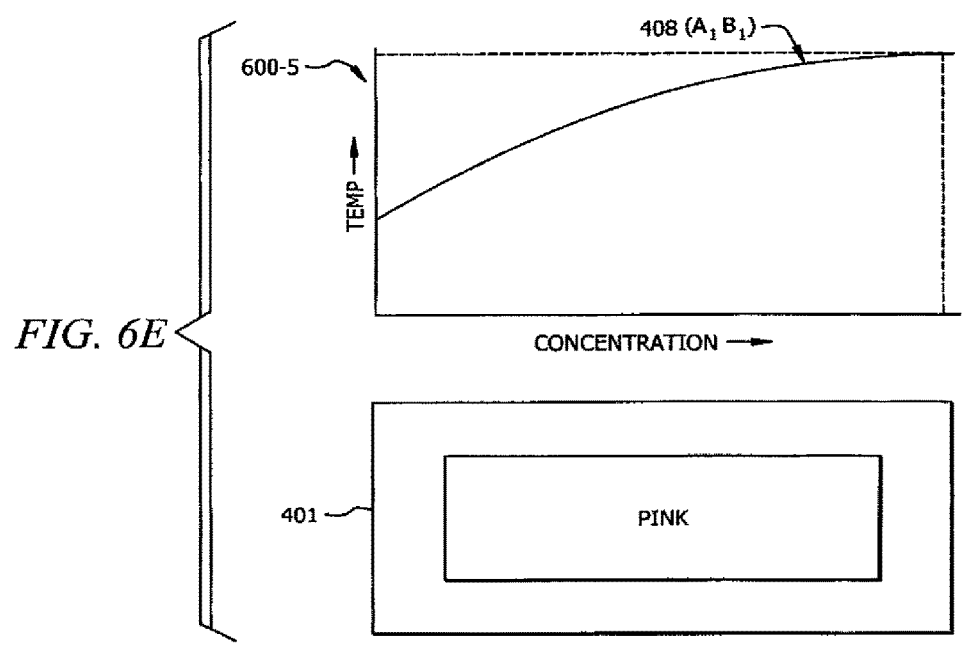

FIGS. 6D-E show this phenomena proceeding with increasing temperature until all of the coating becomes pink in FIG. 6E. Graphs 600-1 to 600-5 shows the point of the color change on the temperature vs. concentration curve as the color changes progressively in FIGS. 6A to 6E respectively. An important aspect of embodiments of this invention is that when a color change occurs in the coating on reaching a particular temperature, if the temperature were to then decrease, the color of the coating would not change back from pink to blue.

In some embodiments, methods of the invention include printing a plurality of indicator precursor compositions on a substrate, wherein each of the indicator precursor compositions is placed on a different portion of said substrate and wherein each of the plurality of indicator precursor compositions permanently changes color in response to exposure to a particular value of said condition. Such methods may include positioning a material with respect to each of the printed indicator precursor compositions for preventing the indicator precursor compositions from changing color in response to exposure to a particular value of the condition until after activation of the precursor composition. Where the condition of interest is temperature, the method may include reducing a temperature of the substrate to a critical temperature below a lowest temperature value which will cause any of the to be produced indicator compositions to change color; and polymerizing the applied precursor compositions after said substrate has been lowered below said critical temperature. In some embodiments, the plurality of indicator precursor compositions is created by placing a layer comprising a first monomer on top of another layer comprising another monomer, and subsequently polymerizing the monomers, wherein at least one of the layers comprise said miscible monomer in varying proportions along the layer. In some instances, the plurality of ink compositions is created by placing a layer comprising one of the monomers adjacent to another layer comprising another of the monomers; and allowing the layers to migrate into each other and polymerizing the monomers, wherein at least one of the layers comprises a monomer in varying proportions along the layer.

In some instances, printing methods are employed which include the steps of: creating an image on a printing apparatus (e.g., a printing plate, a rotogravure cylinder, an ink jet printer) for each ink to be printed; positioning each said ink image in sequential order on a web press; placing each said ink in a separate cartridge and programming each said ink to print sequentially on a substrate; and allowing the printed ink to dry on said substrate. In some instances, printing methods are employed which include the steps of: creating an image on a screen fabric for each ink to be printed; printing in sequential order each said silk screen containing an image; placing each said ink in a separate cartridge and programming each said ink to print sequentially on a substrate; and allowing said printed ink to dry on said substrate.

UV/Liquid Crystal Temperature Modifications:

Liquid crystals and cholesteric liquid crystals, can be utilized in conjunction with co-topo-polymeric compositions and in combination with UV treatment to further adjust, modify, manipulate, up shift, down shift, or change a pre-determined temperature setting for a given co-topo-polymeric composition. Liquid crystals can be modified in their temperature settings by exposing pre-printed materials to ultra-violet light intensities. By doping liquid crystal compositions in co-topo-polymeric compositions, the UV dependent temperature adjustment that affects the liquid crystal composition can be utilized to further facilitate and modulate the transition of the admixed co-topo-polymeric composition.

Such post printing modifications will find use for further changing intrinsic temperature setting of the co-topo-polymeric composition. Likewise, the post UV processing step takes advantage of existing printing and UV exposure processes utilized by the high volume printing industry.

Practical UV intensities can range from 0.1 watt per square inch to over 10,000 watts per square inch, such as from 1 watt per square inch to 5,000 watts per square inch, including from 100 watts per square inch to 2,500 watts per square inch necessary to modulate the physical/chemical composition and proportionately the temperature modulating effect of a liquid crystal component in the composition that in turn effects the temperature setting of a co-topo-polymeric composition.

Utility

Co-topo-polymeric indicator compositions and related active agents find use in a variety of different applications, including but not limited to: early stage production, manufacturing, or synthesis stages through to end-of-use indication where a product or good being monitored using an indicator or composition has already expired and is no longer of any further utility or value.

Co-topo-polymeric indicator compositions find use for a wide range of temperature, sensing, indicating, measurement, dating and marking, cold-chain-management (e.g., for cold-storage items, such as frozen foods, gel packs, etc.), perishable composition monitoring, safety, sensitizing, industrial, food service, pharmaceutical, industrial, processing, food processing, medical and other market and/or product applications.

Co-topo-polymeric indicator compositions find direct utility with and have application to monitoring and reporting storage conditions any product, material, or object where maintaining storage conditions of that product dictate the viability, perishability, freshness, temperature (e.g., food or beverage temperature sensor, such as a coffee sensor configured to provide an indication of reaching a temperature ranging from 37-41° C.), well being, stability, condition, viability, integrity, or any other general parameter that imparts the quality and status of the product, material or object.

Co-topo-polymeric indicator compositions for monitoring an object's or product's condition can be incorporated in a device that attaches to the product of interest or is distal to the product being monitored. The indicating composition can be printed directly on the product or object or be applied in a film or device form. The application of interest will dictate the means by which the indicating composition will be utilized. For example, perishable dairy product will find use with an indicator attached to the product so that the viability and temperature integrity of the product can be visualized form the point of manufacturing, throughout production and further processing and packaging, through storage, through inventory, through transport and logistics, through docking and inspection, through delivery, through storage and display, and through final pickup and handling by a consumer or intended user of the product or object.

Single or pure compositions disclosed herein can be utilized alone or in conjunction with mixed systems. The exact composition and concentration utilized will depend on the temperature setting of interest, material attributes such as stability and color development, processing utilized, processing requirements such as solubility and printing vehicle type, augmenting agents required along with a finished ink composition and the like.

Co-topo-polymeric compositions enable the protection of products, materials, personnel, goods and the like an ongoing, convenient, and direct means for determining a history of temperature violations. Additional product, market, production, and company opportunities that find need for rapid low temperature monitoring include but are not limited to military goods (e.g., munitions, ammunition) that need to be stored at ambient temperatures, vegetables that may harbor pathogens, case ready foods that are either pre-cooked or not, disposable and reusable packaging including pre-molded or thermo formed packaging used for foods or other perishables, the packaging industry, blood bags and the medical industry for safety and storage, a biologic (e.g., blood, animal tissue, organ), donated body parts for the medical industry, flowers and the flower industry for transport and storage, seeds and the seed industry, plastic shrink wrap films that need temperature control during shipping and storage, beer and wine among other alcoholic beverages that require defined storage and shipping temperatures, non-alcoholic beverages (e.g., non-alcoholic beverage having a dairy component, juice) electronic components and technology industries that require temperature control on specialized parts, rare chemicals and the chemical industry, biochemicals and the biotechnology industry, medications both over the counter and prescribed, dairy products including milk, cheese, and ice cream, hummus, red meat, eggs, fruit, a sandwich and other perishable foods, film and papers for the photographic industry, shellfish and other fish for the fish industry (e.g., utilizing a compression indented expanded plastic structure), and the like. Of interest are insertable probes that penetrate netted and packaged products (e.g. shellfish temperature sensors).

Compositions of the invention also find use in monitoring function of various devices or instruments that are required to provide defined temperatures. For example, compositions of the invention may be employed as dishwasher temperature indicating barcodes for recording that commercial and residential dishwashers are functioning according to temperature specifications. Analogous applications include use of analogous indicating barcodes for other types of devices, e.g., refrigerators, thermal cyclers, etc.

Printed Products

Embodiments of the invention include printed products for indicating a maximum level of a condition (e.g., temperature) to which said printed product has been exposed, where the printed product includes a substrate; and a plurality of printed ink compositions wherein each of the printed indicator compositions is placed on a different portion of the substrate, and each of the plurality of indicator compositions permanently changes color in response to exposure to a particular value of the condition of interest. In some instances, the printed product may include a material disposed with respect to each of the printed indicator compositions for preventing the indicator compositions from changing color in response to exposure to a particular value of said condition until after an activation, e.g., via polymerization, has occurred. Printed products of interest include, but are not limited to: labels, product packaging, disposable thermometers, etc. As reviewed elsewhere, the substrate may vary, where substrates of interest include, but are not limited to: paper, film, foil, textile, fabric, plastic, parchment. In some instances, the printed product is configured so that the color change occurs after said printed product has been exposed to said condition for a minimum predetermined time.

Machine-Readable Chemistries and Device Configurations:

In certain embodiments, indicator compositions of the invention find use in machine-readable applications. Machine-readable chemistry and device configurations can include, but are not limited to, various printed barcodes, Interactive barcodes, abuse security barcodes; 1D, 2D, and 3D; barcodes holographic barcodes, vision imaging systems, transient barcodes, time-only barcodes, freshness indicating barcodes, shape memory bar codes, and a variety of other applications and formats.

Compositions herein can be formulated and utilized in a variety of visual, scanning, imaging, and machine readable processes as they relate to temperature monitoring algorithms. Messages or codes can be made to appear or disappear; parts or elements of graphics, symbols or codes can be utilized to make the element, graphic, or code un-discernable or unrecognizable until that portion of the medium has changed with temperature or the like.

Co-topo-polymeric indicator compositions can be utilized in both visual and machine aided formats. Visual readings are made with distinct visual determination of a threshold color change that occurs. Machine aided formats are made using an optical or electrical interpreted change in a color hue or conductive characteristic in a co-topo-polymeric composition that undergoes a state threshold change. By way of example, but not limitation, a composition can be printed or formulated in a machine viewable format. A measurable reading may be taken of an initial colorimetric state. A second or sequential reading can be measured as threshold state occurs. During the transition from one state to another state, an instrumented reading can be registered. The threshold transition can be measured against a calibrated reading such that the degree or magnitude of the state threshold change can be recorded and monitored. Recorded and monitored machine measurements can be displayed by instrumentation utilized in the machine aided format.

Machine readable/responsive barcodes can be utilized for determining the presence of or responding to a temperature fluctuation, visible light, ultra-violet light, irradiation for applications such as food sterilization including gamma and cobalt 60 irradiation levels, hydration, pressure changes, high pressure events including high pressure sterilization, contaminations such a heavy metal contamination, alcohol levels, poisons, chemical sensing, biological compositions, chemical reagents, non-specific analyte binding, specific analyte binding, gases, physical and mechanical responses, UV intensity, light intensity, sanitization conditions, mechanical stress conditions, pressurization formats, oxidation state, optical bleaching, end-of-use indication, time, time and temperature, free radical content, hydration state, skin care health, medical sterilization, clinical health status, indicating sensors on food storage containers medical status, security applications, anti-tampering applications, and any of a number of other measurable indicia.

Machine readable codes for indicating time duration for product shelf-life and use indication can be accomplished using sensing compositions that shift spectrally in response to ambient conditions and product storage.

Also of interest are barcodes embedded or obscured with a co-topo-polymeric indicator composition that is selectively revealed upon triggering at set points of co-topo-polymeric indicator.

A range of barcode languages can be utilized that can be partially of fully associated with a co-topo-polymeric composition and therefore act as a machine readable indication means to measure and report the selective functionality intended to comprise the co-topo-polymeric composition used for indication. Barcode types include, but are not limited to any language, a wide range in size and numbers of character, as well as the barcode language of interest: 39, 93, 128A, 128B, 128C, A standard barcode or UPC code can be obscured, coated, embedded in or over-laid by a mixed or single component chromic change agent. Part of the standard bar code can be clearly visible at the beginning of reading so as to generate an initial starting parameter set. Selective portions of the barcode can be covered by discrete compositions that are set to change color at pre-determined temperature exposures. As the barcode is placed on a product type at a lowered temperature the chromic change agent can be activated. On activation, pre-determined elements of the code will be obscured by the optical density of the chromic change agent (i.e., the co-topo-polymeric indicator composition). The optical density of the barcode will be set such that a barcode reader will not be able register the obscured portion/bars that represent a specific code sequence. As the barcode/product is raised in temperature and as pre-selected temperature are achieved and exposed, a pre-determined section of bar code will be revealed (reversibly or irreversibly depending on the nature of the chromic change agent selected). As each temperature threshold is achieved during the temperature exposure process, each pre-determined/coated barcode region will be come machine readable. In some instances, an indicator may be configured as a linear segmented barcodes that differentially respond to temperature and/or time-temperature along their axis.

Non-readable or partially readable barcodes utilizing single or mixed compositions (e.g., polydiacetylene compositions) as the obscuring agent are readily scanned for activity or inactivity in part or in whole.

Polydiacetylenes and other blue/black bar codes provide a unique optical masking characteristic that makes a partially readable of fully non-readable part or all of the modified bar code. In addition the transition of a blue/black polydiacetylenic compound to a red or orange hue including but not limited to light pink to dark red hues, provides for high optical readability by most commercial barcode readers since the red, orange, pink or related hues are optically transparent to the red light sources utilized in standard barcode readers.

Readable barcode languages include but are not limited to: Morovia Code 25, 11, 12B. 139. UPC-A, UPC-E, EAN-8, EAN-13, code 128b, USS 39, USD 3, 3 of 9 code, code 39. hibcc. Java applet, logmars, full, symbology, industry 2 of 5, discrete, self checking codes, msi, plesssey, one-dimensional barcodes, two-dimensional barcodes, three-dimensional barcodes, halographic barcodes, luminescent barcodes, and the like.

Barcode formats of interest include, but are not limited to: Off to On switching barcodes; On to off switching barcodes; Codes 39 and 93 for embedded thermal messaging; various barcode geometries, such as planar, curved, round, etc.; barcodes configured for thermal delay for time temperature coding; freshness indicating barcodes; time-only indicating barcode; etc.

In some instances, one may have re-programmable barcodes that can be re-set among, in between or adjacent to a bar code set through re-printing a region of interest.

Thermal Delay Timing and Mechanisms:

In some instances, product devices and applications are employed where there will be either no thermal delay or thermal history mechanism in the color change process embedded in a device, a minimal delay mechanism or history in the color change process, or a prolonged delay in the color change process. Non-delay to delayed timing can range from 0.01 seconds to over 6 months. Delay durations required may range from between 0.1 second and 3 months. Timing delays may range between 1 second and 1 month. Delays designed into devices utilizing indicating compositions may range between 3 seconds and several days. The actual desired delay timing and mechanism for incorporating the delay will be selected based upon specifications for the intended product.

Thermal delay mechanisms can include, but are not limited to, chemical means, physical means or a combination of both. Physical thermal delay mechanisms can include insulation methods, thermal conductive mechanisms, or a combination of both, e.g., heat-sink/insulator designs.

Multi-Plexing Co-Topo-Polymeric Indicator Compositions and Responses with Other Indicators:

Other existing temperature monitoring devices can be modified to include the disclosed co-topo-polymeric indicator compositions for low temperature monitoring. By way of example, a "Pop-Up" temperature indicator (Volk Enterprises, Inc. Turlock CA, USA) can be modified to include the disclosed co-topo-polymeric indicator composition on the external stem portion of a Pop-Up temperature indicator, such that the low-temperature indicating composition acts as low-temperature indicator during storage of a meat, e.g., cow, pork, game, etc, poultry or other food product that includes the Pop-Up temperature indicator device. The Pop-Up device can conveniently act as an anchoring point for the low temperature indicator as well as a means to keep the low temperature indicator in thermal contact with the food product.

Refrigerator thermometers, analog and digital meat thermometers, disposable cooking sensors, and various other temperature indicators can be modified to contain a sensor or indicator comprising a co-topo-polymeric indicator composition of the invention for low temperature indication. In some instances, applications may employ the use of an integrated barcode reader (for reading a barcode embodiment of the co-topo-polymeric indicator)/digital thermometer for simultaneous real-time/historical temperature reading in a single measurement.

Low temperature indicating compositions disclosed here within can be readily utilized with food service label materials such as dissolve-away labels utilized in food handling (DayMark Corporation, Bowling Green Station Ohio, USA). The low-temperature co-topo-polymeric indicator composition can be conveniently imprinted on a dissolve-away label substrate and attached to a food product or carrier of chilled food products such that its activity can be monitored for temperature indication as well as be disposed of as the dissolve-away label is removed during cleaning or the like. In yet other embodiments, compositions of the invention may be directly printed on food for reporting food status:

A range of TTI (time-temperature indicators) can be multi-plexed with or adjoined with devices and indicators utilizing co-topo-polymeric indicator compositions. Devices can include, but are not limited to, those that are sold commercially such as and by way of example ATI, Ciba, Avery, Patel, DayMark, and the like. A portion or region on such devices can be modified with the disclosed co-topo-polymeric temperature threshold indicating compositions such that an additional unanticipated sensing element can be included in current commercial or development based products.

Thermal Time Delays Using Recessed Configurations:

Recessed thermal delay configurations can be used in combination sensors whereby the same sensor can be used for low-temperature threshold measurement and high temperature cooking measurement. By way of example, a recessed device can have at it lowest inner indented region a printed area containing a low temperature co-topo-polymeric indicator composition. The plastic recessed device portion of the product can be made using a thermoformable polystyrene that is heat stressed during the thermoforming process. After a threshold temperature has been monitored and the product is intended to be cooked, the thermoformed device region can be made to respond to external cooking temperatures through a conformational relief structure change from a recessed configuration to a planar configuration.

Thermal/time delay mechanisms can include configurations that place the low temperature sensing composition recessed within the thermal mass of a product whose temperature is being monitored. The device configuration can be indented such that the sensing region is below the surface plain of the product. Configurations can include, but are not limited to thermoformed indents, injection molded indents, pressure formed indented devices, and other molded or manufactured parts that provide for good thermal contact with a product such that the sensing region is recessed internally to the product.

The recession depth into a product being monitored can range from 1.0 millimeters to 10 centimeters, such as from 2.0 millimeters to 5 centimeters and including from 3 millimeters to 3 centimeters, e.g., from 0.5 centimeters to 1.5 centimeters.

Thermal delay configurations for devices can be designed and made with a variety of plastic types including but not limited to: polyvinyl chloride (PVC), various polyolefins such as polypropylene and polyethylene, high density polyethylene (HDPE), low density polyethylene (LDPE), crosslinked high-density polyethylene (XLPE), softened acrylic, ABS, thick Kapton™ tape materials, Teflon® (polytetrafluoroethylene (PTFE), tetrafluoroethylene TFE and fluorinated ethylene polyproplyene FEP)-based materials, brand names such as Kydex, high to low impact polystyrene, thermoplastic polyesters, nylon, styrene-butadiene, epoxy casts, polybutylene, TPX (poly(methyl pentene), terephtalate polyethylene (PET), PETE, PETF, polyethylene teraphthalate G copolymer (PETG), polysulfone (PSF), polyutethane (PUR) Thermanox™ (TMX), polymethylmethacrylate, and the like. Strong flexible plastics such as polycarbonate are often desirable. Polycarbonate can be thermoformed, pressure formed, and injection molded.

Other exemplary plastics may include, but are not limited to: ethylenechlorotrifluoreethylene (ECTFE), ethylentetrafluorethylene (ETFE), polinvinylidene fluoride (PVDF), ethylene-propylene rubber (EPR), silicone rubber (SI), Alcryn® thermoplastic rubber (TPR), HT thermoplastic rubber (HTPR), Santoprene® thermoplastic rubber (TPR), LSOH crosslinked compounds, LSOH thermoplastic compounds, methylvinyletherfluoralkoxy (MFA), perflouroalkoxy (PFA), thermoplastic polyester elastomer (TPE), polyimide (Kapton®), polyurethane (PUR), polyvinyl chloride 105° C. (PVC), polyvinyl chloride 70° C. (PVC), low temperature polyvinyl chloride (LTPVC), oil resistant Polyvinyl chloride (OR PVC), semirigid polyvinyl (SR PVC), polyvinyl chloride polyurethane (PVC PUR), and the like. Expanded or foamed plastics can be used to increase or decrease thermal contact accordingly. Expanded plastics can be formed with a variety of different expanding agents including Expancel™ or the like.

Thermal time delay sensor configurations can be designed in a variety of convenient configurations including but not limited round, square, rectangular or other geometric species. Thermal delay device configurations can include thick or thin substrates ranging thickness from 0.001 millimeter to greater than 3 centimeters, such as from 0.01 millimeters thick to 1 centimeter and including from 0.1 millimeter to 0.5 millimeters thick.

Optical Pattern and/or Message Development:

Optical patterns can be developed under triggering conditions using optical color change dye systems in combination with modeled substrate surfaces. An image can be generated by applying a pressure indicating film over a substrate layer that has been pre-surface textured or patterned. As temperatures are induced the dye layer initially comes in contact with the close proximity regions or features of the patterned substrate surface. An initial color change will occur in the dye layer that emulates the upper surfaces of the substrate. As temperatures continue to increase, the dye layer may be forced in contact with lower regions of the substrate surface texture. Images or patterns can appear differentially as a result of the final temperature induced between the temperature indicating dye layer and the patterned or textured substrate. Partial images can be made to occur at lower temperatures. More complete or developed images or messages can be made to appear at medium pressures. Fully developed images or completed messages can be made to appear at final desired induced temperature.

Expiry Date Indicators

One application of interest is the use of the indicator compositions of the invention as product expiry indicators. Such embodiments the problem of "fixed expiry" dates of products by devices and methods that continuously update the expiry date of a perishable product if and as the product is exposed to harsher than expected environmental conditions. The invention involves the use of indicator compositions of the invention in printing products such as labels and packaging materials to achieve this objective. In this embodiments, indicator compositions are configured on a printed product, in a way such that the history of temperature levels to which a product is exposed causes a readable message to be displayed. In one embodiment of the invention, that readable message is an expiry date of a product.

Figure 7A:
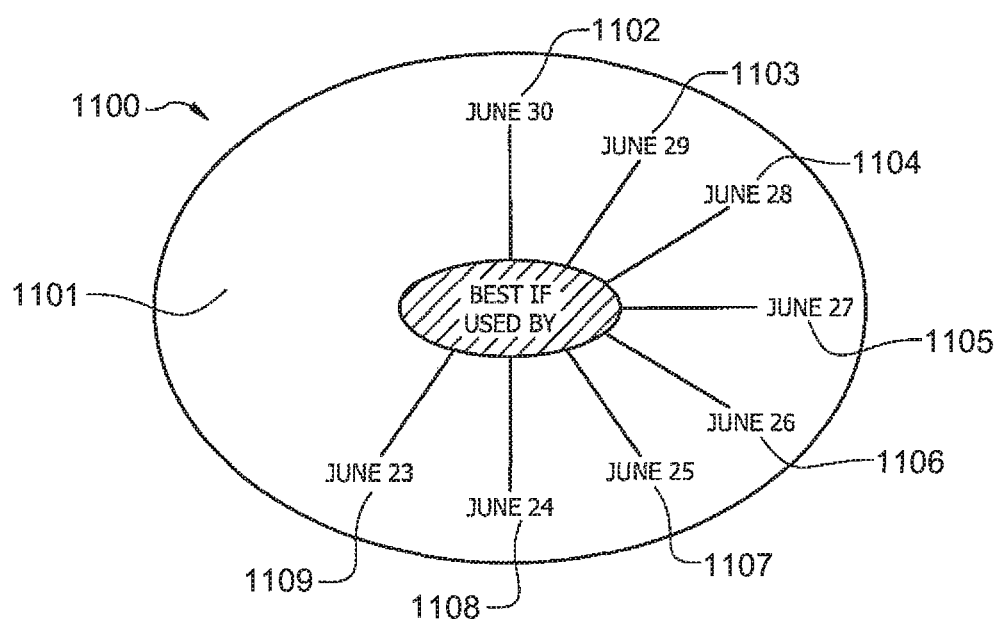
FIGS. 7A to 7C show an embodiment of the current invention displaying readable messages caused by indicator color changes.

FIG. 7A shows an embodiment of the invention label 10 where compositions of thermochromic irreversible ink are used to print expiry dates on product labels. In FIG. 7A, label 1100 is used to label perishable products or to label any object where its temperature history is important to know and track. Label 1100 includes expiry dates 1102 to 1109 disposed on substrate 1101. Substrate 1101 may be paper, film, foil, textile, fabric, plastic, parchment or any such similar material. The thermochromic property of the ink compositions is activated by ultraviolet light. Ultraviolet light is used to activate the thermochromic property when it is time to start tracking conditions that affect quality. The time to start tracking is usually after label 1100 is affixed to the perishable product and the perishable product placed in proper storage. Once in proper storage, the thermochromic property of the ink may be activated by ultra violet light. Preferably, the initial color of the printed expiry dates, except the first expiry date is such as to make printing invisible to the human eye. This can be accomplished, for example, by printing the dates in colorless ink or in the same color ink as the color of the substrate.

The first expiry date 1102 is June 30 and represents an expiration date of the product under optimal handling conditions. This date is visible to the human eye from the outset when the label is first affixed to the product. Expiry dates 1103 to 1109 are initially invisible. Each of the ink compositions of these expiry dates, however, change color at different temperatures or at accumulations of temperatures over a time period. For example, initially, substrate 101 may be white, expiry date 1102 blue and expiry dates 1103 to 1109 colorless (appearing white like the substrate).

Figure 7B:
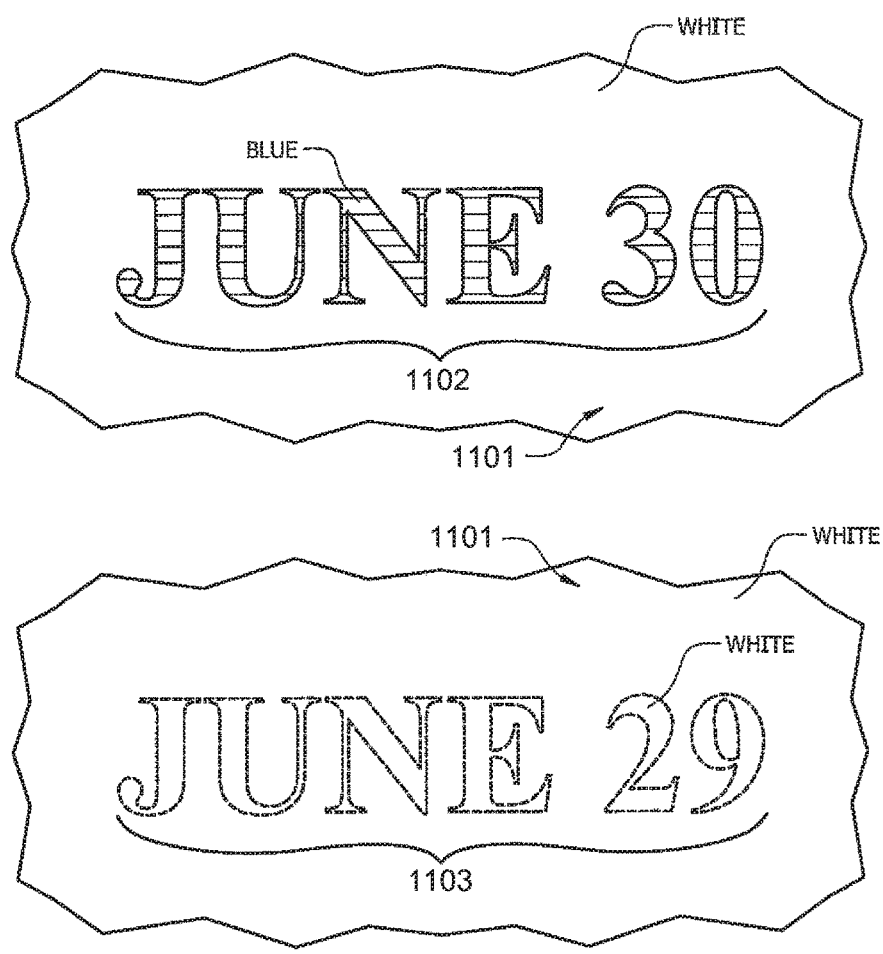

FIG. 7B shows an exploded view of portions of label 1100 when label 1100 is first affixed to the product. Expiry date 1102 is blue and visible against white substrate 1101. Expiry date 1103 is shown in phantom because it is colorless and appears white against white substrate 1101.

The June 29 expiry date 1103 may have an ink composition that changes color to blue if label 1100 is exposed to a temperature of 0° C. for a predetermined time of one hour. If label 1100 is exposed to a temperature of 0° C. for one hour, then the June 29 expiry date 1103 will irreversibly change to a blue color and thereby display a shortened expiry period of June 29.

Figure 7C:
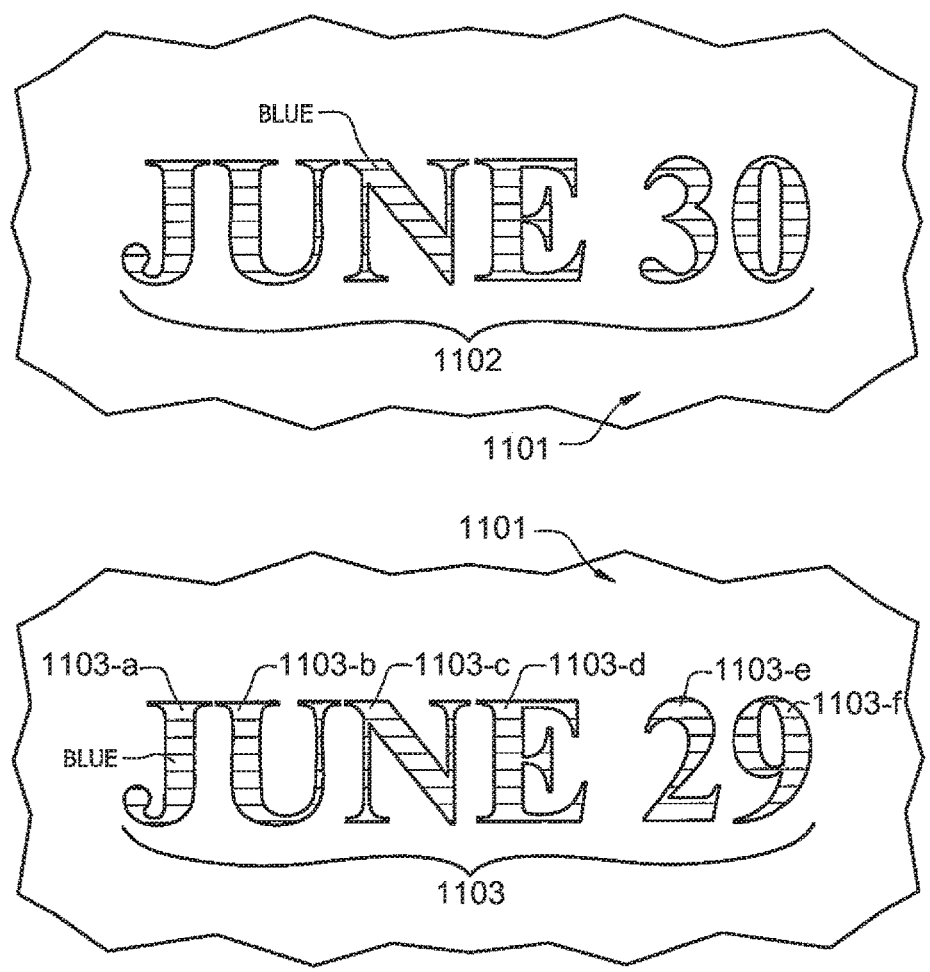

FIG. 7C shows an exploded view of portions of label 1100 after label 1100 has been exposed to a temperature of 0° C. for an hour. Each of printed areas 1103-a to 1103-e is printed with the same composition of irreversible thermochromic ink and, accordingly, has changed to a blue color after exposure to a temperature of 0° C. for one hour. Each of printed areas 1103-a to 1103-e are now visible against white substrate 1101. In sum, the color change of the irreversible thermochromic ink of printed areas 1103-a to 1103-e displays expiry date 1103 which reads "June 29."

Referring to FIG. 7A, the ink composition of the June 28 expiry date 1104 may change color to blue if exposed to a temperature of 10° C. for 30 minutes. If label 1100 is exposed to a temperature of 10° C. for at least 30 minutes then a shortened shelf life will be displayed in the form of the June 28 expiry date 1104.

Similarly, the expiry dates 1105 to 1109 have ink compositions that change color for increasingly harsher conditions. The expiry dates 1105 to 1109 would change color if and when label 10 is exposed to these harsher conditions. Thus, a consumer of the perishable product or a seller of the product may read the label to be advised of the new shortened expiry date if the perishable product is exposed to harsher than recommended conditions. It should be noted that in addition to labels, the printed product could be packaging material used to package perishable products.

Figure 8A:
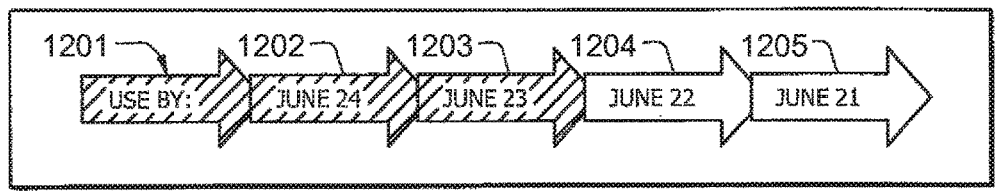
FIGS. 8A to 8C & 9 show embodiments of the current invention using occlusion caused by indicator color changes.

FIGS. 8A to 8C & 9 show embodiments of the current invention where the irreversible thermochromic ink compositions change color to occlude previously displayed expiry dates and thereby communicate the current expiry dates depending on the level of exposure of the product to harsh environmental conditions. In FIG. 8A, expiry dates 1202-1205 are printed with different ink compositions on substrate 1201 in a sequence of arrows. As exposure of the product to progressively harsher conditions occur, the longer expiry dates are occluded by a color change from left to right. The occlusion occurs, for example, because the area surrounding the printed characters change to the same color as the characters.

Figure 8B:
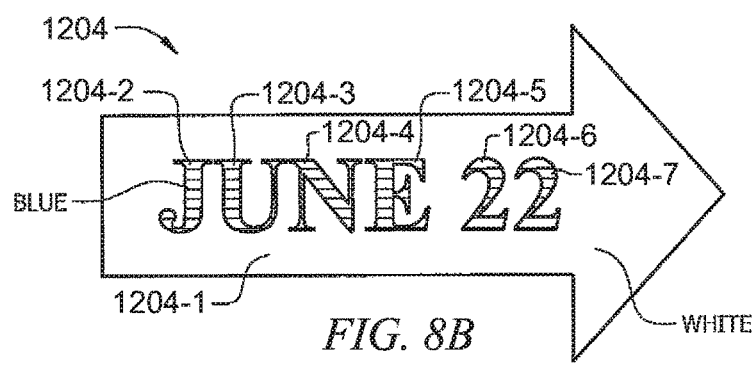

FIG. 8B is an exploded view of expiry date 1204. Area 1204-1 surrounds characters 1204-2 to 1204-7. Characters 1204-2 to 1204-7 may be printed with ink that is not thermochromic. In this example, characters 1204-2 to 1204-7 are printed in blue ink that does not change color with temperature. In contrast, area 1204-1 is printed with irreversible thermochromic ink which is initially colorless and appears white—the color of the area 1204-1. Thus, initially, characters 1204-2 to 1204-7 are visible to the human eye.

Figure 8C:
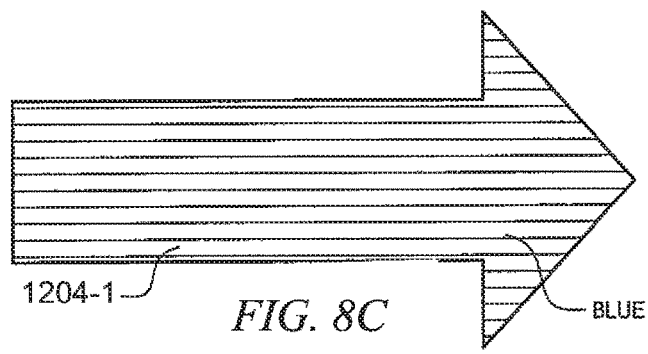

FIG. 8C shows an exploded view of expiry date 1204 after expiry date 1204 has been exposed to a predetermined temperature for a predetermined time to cause area 1204-1 to change color from white to blue. This color change from white to blue, of area 1204-1, causes characters 1204-2 to 1204-7 to become invisible.

Figure 9:
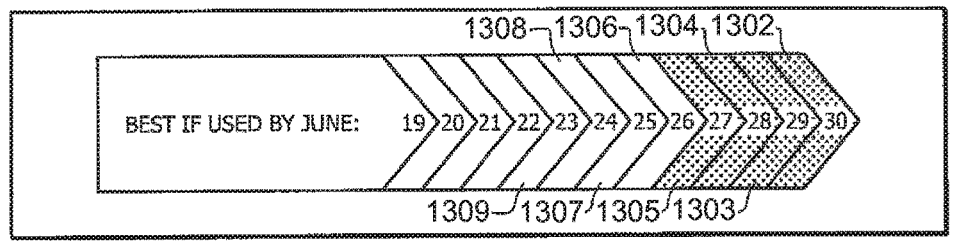

In FIG. 9, a sequence of expiry dates in the form of arrows 1302 to 1309 are being occluded from right to left as the shelf life is exposed to progressively harsher conditions. In this example, a consumer can tell that the current expiry date of the product is June 26.

In some embodiments, the characters displayed by exposure to harsher conditions may be computer readable. The characters may also both be readable by the human eye and a computer. Alternatively, the color change may create lines that display a bar code readable only by computer. That computer readable barcode may be read by a bar code reader which then displays a message to a user. For example, depending on the extent of the exposure of the harsh environmental conditions, messages may be relayed via the bar code reader such as "dispose product," "discount product" or any other such message. It should be noted that the environmental conditions discussed in this disclosure focuses on temperature. However, the principles of the invention are equally applicable to conditions such as pH and humidity.

Figure 10:
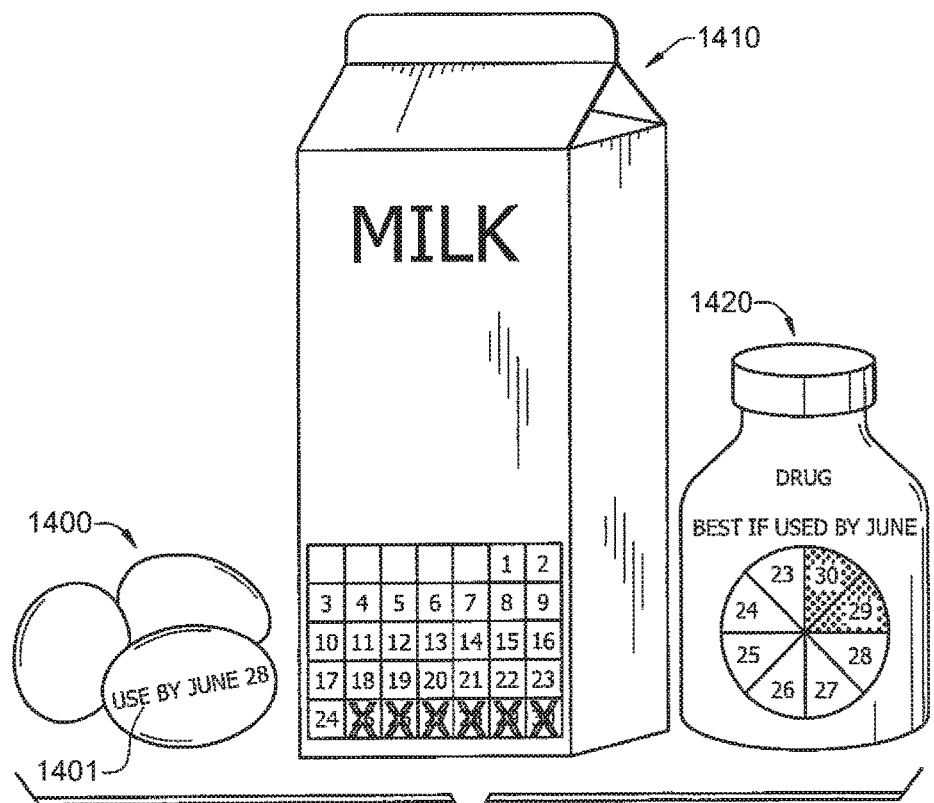
FIG. 10 shows embodiments of the current invention applied to consumer products.

FIG. 10 shows embodiments of the invention in common consumer products. Notably, consumer product 1410 shows that the invention may be applied so that the consumer product itself serves as substrate 1401. In other words, for egg 1400, substrate 1401 is the shell of the egg. Consumer products 1410 and 1420 are a carton of milk and a pharmaceutical product, respectively, displaying configurations of the readable message affixed to the packaging of the product.

Figure 11A:
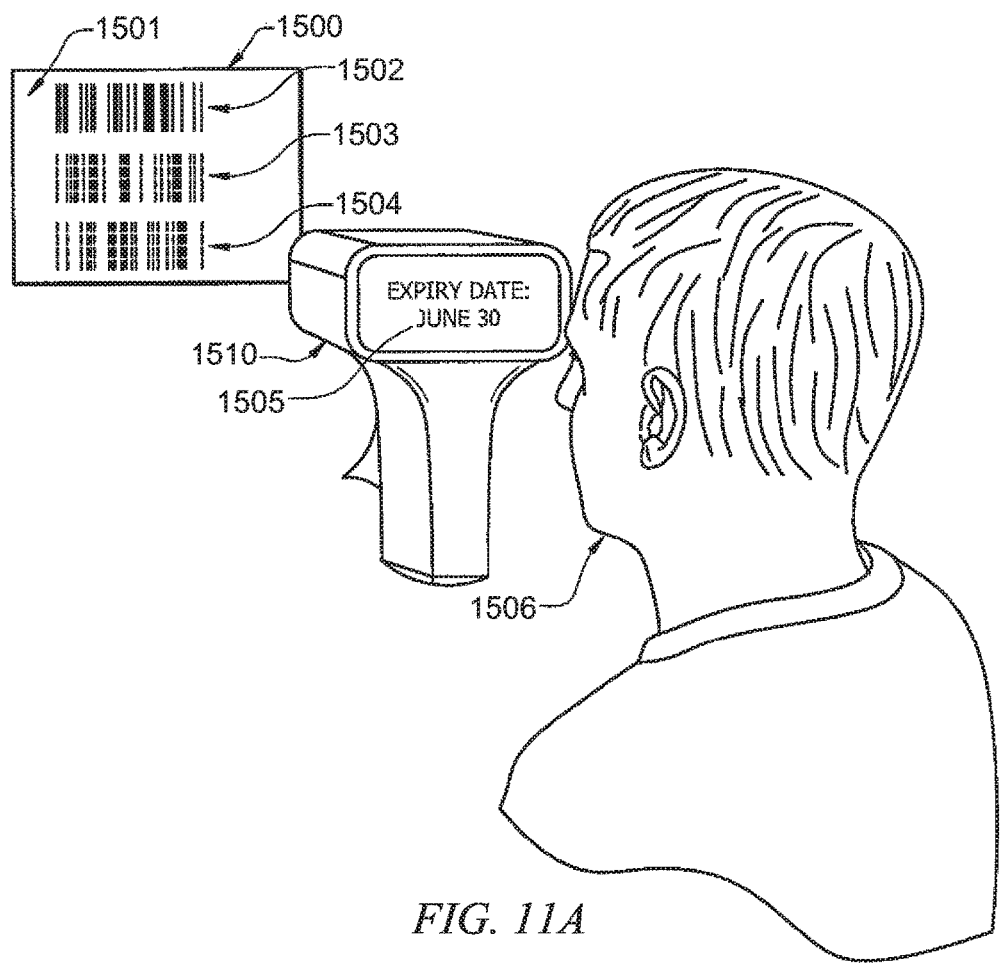
FIGS. 11A to 11C show one embodiment where the expiry date is read by a scanner.
Figure 11B:
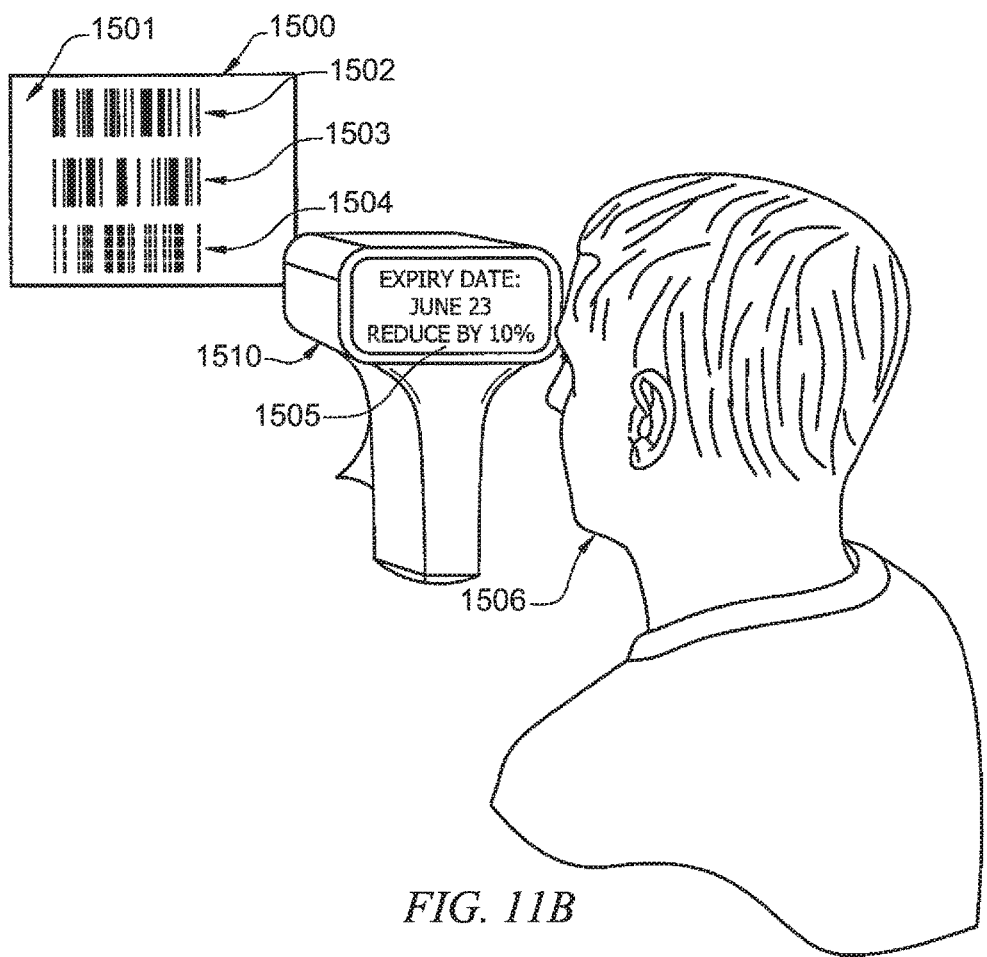
Figure 11C:
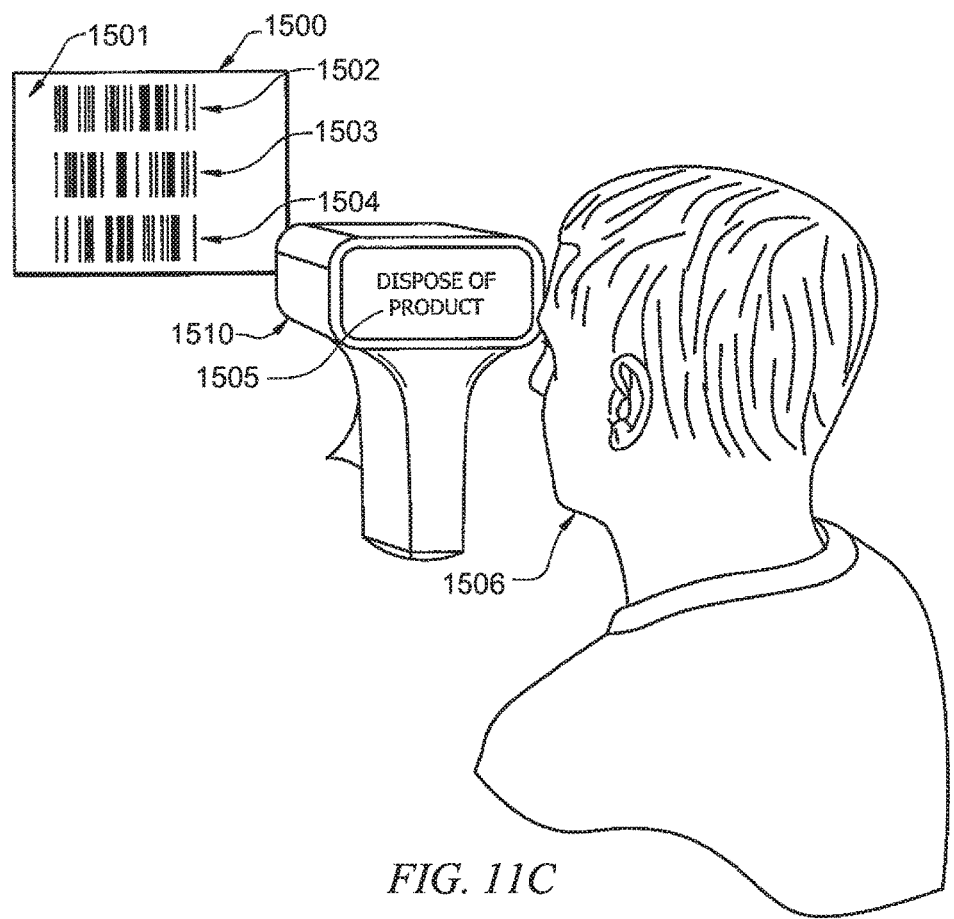

FIGS. 11A to 11C show one embodiment where the expiry date is read by scanner 1510. In FIG. 11A, label 1500 has substrate 1501 with barcodes 1502 to 1504 printed with different compositions of irreversible thermochromic ink. Bar codes 1502 to 1504 are scanned and interpreted by scanner 1510. In turn, scanner 1510 displays a message based on the bar codes scanned. Bar codes 1502 to 1504 are displayed and may be read by scanner 1510 only when the ink composition of that particular bar code has been exposed to a predetermined level of temperature for a predetermined time. When bar codes 1502 to 1504 are displayed because of a color change of the barcodes' irreversible thermochromic ink, the displayed bar codes 1502 to 1504 are unintelligible, though visible, to user 1506. Barcodes 1502 to 1504 are consecutively displayed as label 150 is exposed to progressively harsher conditions. FIGS. 11A to 11C depict label 1500 exposed to progressively harsher conditions.

FIG. 11A shows bar code 1502 displayed. Bar code 1502 is detectable by scanner 1510. Bar code 1502 is also visible but unintelligible to user 1506. Bar codes 1503 and 1504 (shown in phantom) are not detectable by scanner 1510 or visible to user 1506 because label 1500 has not been exposed to the conditions that would change the color of the ink in bar codes 1503 and 1504. On the other hand, bar code 1502 changes to a different color from the color of substrate 1501 when the thermochromic properties of label 1500 is activated and the product to which label 1500 is attached is moved from a main storage (where the temperatures are relatively cold) to a display shelf where the temperature is still cold but relatively warmer than the main storage. When label 1500 is scanned by scanner 1510, therefore, scanner 1510 displays message 1505 which reads "Expiry date: June 30." The expiry date of June 30 represents the expiry date of the perishable product if the perishable product is stored under optimal conditions. User 1506, having read message 1505, can use this information to sort products on a display shelf in terms of date.

FIG. 11B shows bar codes 1502 and 1503 displayed. Bar code 1503 is made of thermochromic ink compositions that changes color on exposure to conditions that are less than optimum but not enough to completely deteriorate the perishable product. It should be noted that scanner 1510 would be programmed so that when a label is scanned by scanner 1510, the message displayed by scanner 1510 is relevant to the most recently displayed bar code. This may be done by different ways. For example, scanner 1510 may be programmed to display the message pertaining to the barcode with the most lines. The bar code with the most lines represents the bar code pertaining to exposure to the most severe conditions. In FIG. 11B, because of the exposure to less than optimum conditions, scanner 1510 can now read bar codes 1502 and 1503. However, because barcode 1503 has more lines than bar code 1502, message 1505 pertains to bar code 1503 only. In this example, the expiry date in message 1505 changes from June 30 to expiry date June 23. Additionally, message 1505 advises user 1506 to reduce the price by, say 10%.

FIG. 11C shows bar codes 1502 to 1504 displayed. Bar code '504 has irreversible thermochromic ink that changes color when label 1500 is exposed to a temperature level and for a time that deteriorates the perishable product to a level where the perishable product should be disposed. After exposure of the perishable product to this detrimental condition, the thermochromic ink in bar code 1504 changes color displaying bar code 1504. After the display of bar code 1504, because of a change in the color of ink, scanner 1510, when used to scan label 1500, will display a message pertaining to bar code 1504. The message displayed now pertains to bar code 1504 and not bar codes 1502 and 1503 because bar code 1504 has more lines than bar codes 1502 and 1503. Here, the message displayed is "Dispose Product."

The embodiments of the invention shown in FIGS. 11A to 11C involve a hand-held scanner that detects and reads the bar codes formed by color changes of thermochromic ink. However, in another embodiment, the shelves that store perishable products may contain the scanning apparatus that automatically scans the bar codes as the bar codes are formed due to color changes caused by changing environmental conditions such as temperature. The information that these bar codes provide with regards to the environmental conditions in which a product is stored may be sent to a central processing station and used for inventory management, detecting equipment problems and the like.

Embodiments of the invention as illustrated in FIGS. 11A to 11C may also help in product quality management procedures pertaining to the receipt of product by an entity in the chain of supply. For example, scanner 1510 may be used to scan pallets of products on delivery to a retail store. Before accepting the pallets of products from a trucker and stacking them on shelves for purchase by consumers, receiving personnel may use scanner 1510 to scan bar codes, formed by color changes of irreversible thermochromic ink located on the labels of the products. It should be noted that although bar codes are discussed in several embodiments of this disclosure, the irreversible thermochromic ink may be printed to display any type of code, symbol or character that may read or interpreted by a human or a computer.

Figure 12:
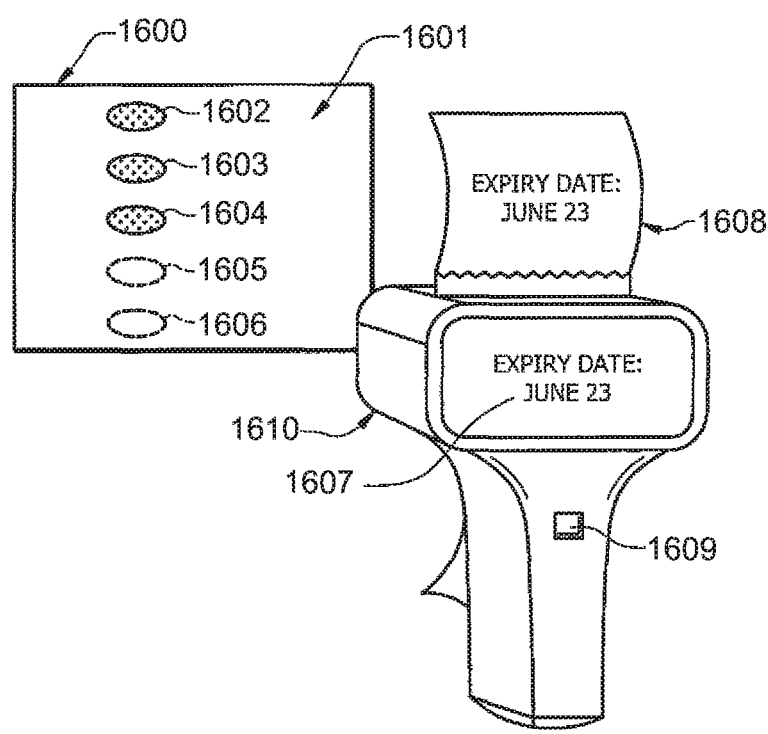
FIG. 12 shows one embodiment of the invention that prints current expiry dates.

FIG. 12 displays label 1600 used for labeling a perishable product. Machine readable characters 1602 to 1606 are printed on substrate 1601 and have different compositions of irreversible thermochromic ink. As the perishable product to which label 1600 is affixed is exposed to progressively more severe temperatures, more of readable characters 1602 to 1606 change color. In this example, the perishable product has been exposed to the temperatures that would cause each of the ink compositions in readable characters 1602 to 1604 to change color. Characters 1605 and 1606 are not detectable by scanner 1610 because the perishable product has not been exposed to temperature conditions that would cause the ink in characters 1605 and 1606 to change color. When scanner 1610 scans label 1600, therefore, it detects characters 1602 to 1604 and displays a message 1607 corresponding to the condition of the perishable product when it has been exposed to conditions that causes the thermochromic ink in characters 1602 to 1604 to change color. Additionally, a user may opt to have scanner 1610 print label 1608 that gives a new expiry date. In this example, label 1608 reads "Expiry date: June 23."

It should be noted that scanner 1610 may have a thermometer 1609 that checks the temperature of the immediate surroundings of the perishable product when label 1600 is scanned. This temperature could be used in conjunction with the information derived from readable displays 1602 to 1606 to establish what the expiry date should be. For example, the harsher the temperature of the immediate surroundings, or the outside temperature as received or measured by scanner 1610, the closer the expiry date would be set. The scanner could also print a label "Dispose Product" if it detects readable displays that indicate that the perishable product has been exposed to conditions that makes it unfit for use.

Figure 13:
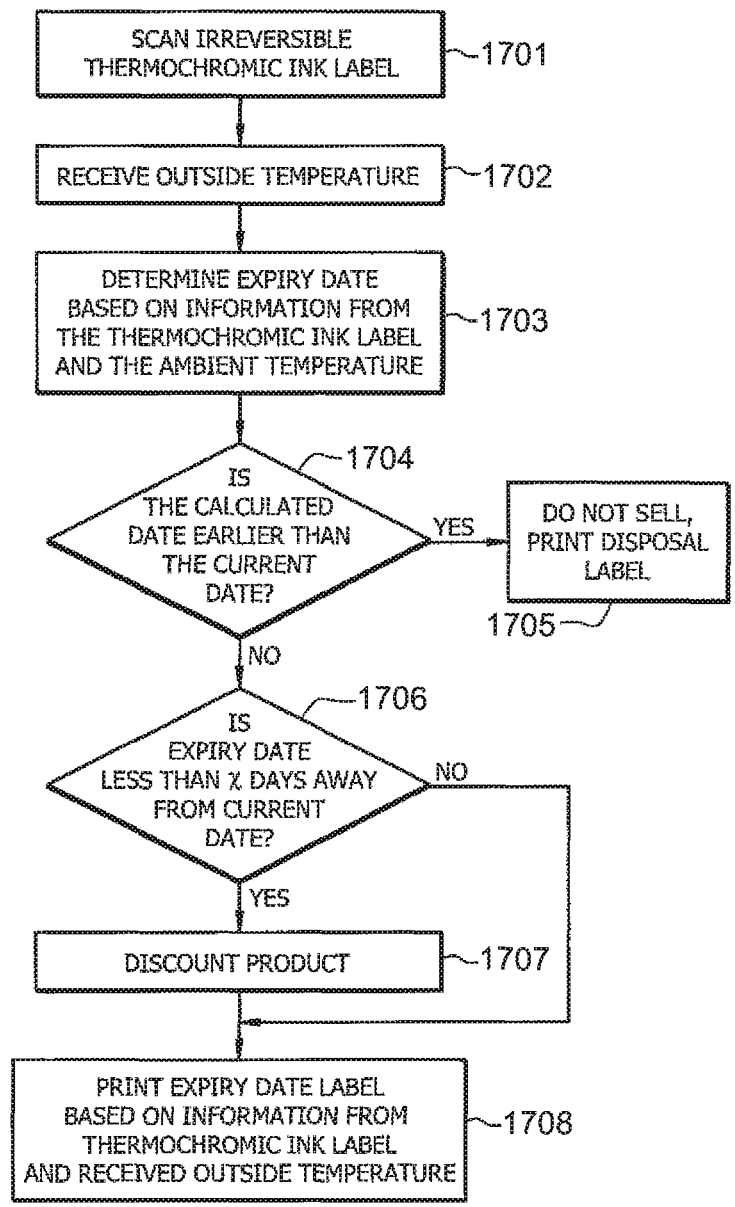
FIG. 13 shows a flow chart of one embodiment of the invention.

FIG. 13 shows one embodiment of the current invention where the expiry date of a perishable product is determined from information provided by an irreversible thermochromic ink label (for example by bar codes as discussed above) and information received about an outside temperature. The perishable product has a label with bar codes of different compositions of thermochromic ink. Each composition changes color after exposure to a predetermined temperature for a predetermined time. In process 1701, a scanning machine at a checkout counter scans product bar codes for prices and thermochromic ink bar codes related to the conditions to which the perishable product has been exposed. In process 1702, the system receives the temperature that exists outside of a store. The system then uses the thermochromic bar codes and the received outside temperature to determine what the expiry date of the product should be. In other words, in winter the expiry dates would tend to be longer than the expiry dates in summer because the exposure to heat during transportation to the home of a consumer is more detrimental in the summer.

In process 1704, the system asks whether the calculated date is earlier than the current date. If the calculated expiry date is earlier than the current date, the system displays a warning not to sell the product and may print a "Product to be disposed" label in process 1705. If the calculated expiry date is not earlier than the current date, then the system asks whether the expiry date is less than x days away from the current date. If the expiry date is equal to or above "x" days from the current date, then the product quality has not significantly deteriorated by previous storage conditions. Thus, the applicable expiry date is printed in process 1708. If the expiry date is less than "x" days away from the current date, then the system discounts the product in process 1707 because substantial deterioration has occurred. In addition to the product being discounted, the system prints an expiry date label reflecting a closer than normal expiry date in process 1708.

As such, embodiments of the invention include a printed product for dynamically communicating the exposure of the printed product to harsh environmental conditions, where the printed product includes a substrate; and a plurality of printed indicator compositions wherein each of the printed indicator compositions changes color on exposure to predetermined levels of an environmental condition, where the indicator compositions are configured to display a readable message on exposure of the printed product to the predetermined levels of said environmental condition. In some instances, the readable message is an expiry date. The substrate may vary, where examples of suitable substrates include paper, film, foil, textile, fabric, plastic, parchment, a consumer product. In some instances, the printed product is a label or a product package. The environmental condition may vary, where in some instances the environmental condition temperature, humidity or pH. In some instances, the readable message is capable of being read by any selection from the list consisting of: a human, a computer, a scanner. In some instances, color change occurs after said printed product has been exposed to said condition for a minimum predetermined time.

Aspects of the invention further include methods of determining exposure of a consumer product to environmental conditions, where the methods may include affixing a printed label to said consumer product, and displaying a permanent readable message on exposure of the printed label to a predetermined level of an environmental condition. Aspects of the invention further include methods of monitoring the expiry date of a product, where the method includes scanning a character formed by changes in color of an irreversible indicator composition on the product using a scanning device adapted to read and interpret said character. In some instances, the character is a bar code and the device is a bar code reader. In some instances, the device communicates a message, readable by a user, based on said character formed by changes in color of irreversible thermochromic ink. The message may vary, and in some instances is an expiry date, pricing instructions, stacking instructions, disposal instructions, equipment failure notification. In some instances, the scanning device prints a label based on information from said scanned character formed by changes in color of irreversible indicator. In some instances, the scanning device is located in an apparatus for storing said perishable products. In some instances, the method further includes receiving and processing a temperature of the perishable product's immediate surroundings.

Aspects of invention further include methods of establishing the expiry date of a perishable product, where the methods include scanning a display formed by color changes of irreversible indicator; receiving a measured temperature; and determining the expiry date from information obtained from said scanned character and a received measured temperature. In some instances, such methods further include determining whether a current date is later than the expiry date. In some instances, the methods further include discounting the product based on said determined expiry date. In some instances, the methods include printing an expiry date label based on the determined expiry date.

The following examples are offered by way of illustration and not by way of limitation.

EXPERIMENTAL

Precursor compositions of various ratios of Me-10,12 C25: Pr-10,12 C21 were prepared as shown in left hand column of Table 3 below. Following polymerization to produce indicator compositions, the initial temperature at which color change occurs (Initial T), the temperature at which color change is half complete (Mid T) and the temperature at which full color change has occurred (Final T) was recorded, as shown in Table 3. The results show that by mixing various ratios of monomers one can obtain indicator compositions having defined, low temperature color change characteristics.

Me-10,12
　C25;
Pr-10,12
　C21

TABLE 3

| % Me C25 | Initial T (F.) | Mid T (F.) | Final T (F.) | Temp Variable (F.) |
| --- | --- | --- | --- | --- |
| 100 | 61 | 67 | 73 | 12 |
| 95 | 54 | 59 | 64 | 10 |
| 91 | 50 | 56.5 | 63 | 13 |
| 83 | 50 | 53.5 | 57 | 7 |
| 67 | 43 | 48.5 | 54 | 11 |
| 50 | 36 | 41 | 46 | 10 |
| 33 | 25 | 31 | 37 | 12 |
| 25 | 12 | 16.5 | 21 | 9 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of detecting the occurrence of a stimulus, said method comprising:
    applying a stimulus to a co-topo-polymeric indicator composition comprising a copolymer of a co-crystallized first alkyl ester diacetylenic acid monomer and a second alkyl ester diacetylenic acid monomer that is distinct from the first alkyl ester diacetylenic acid monomer; and
    assessing said co-topo-polymeric indicator composition for the occurrence of a color change.

2. The method according to claim 1, wherein said stimulus is temperature.

3. The method according to claim 2, wherein said method is a method of determining whether an article comprising said co-topo-polymeric indicator composition as been exposed to said temperature.

4. The method according to claim 3, wherein said article is a food or beverage.

5. The method according to claim 4, wherein said food or beverage is perishable.

6. The method according to claim 4, wherein said article is a food.

7. The method according to claim 6, wherein said food is selected from the group consisting of red meat, fish, shellfish, eggs, a dairy product, a vegetable, a fruit, a packaged prepared food and a sandwich.

8. The method according to claim 4, wherein said article is a beverage.

9. The method according to claim 8, wherein said beverage is selected from the group consisting of an alcoholic beverage, a non-alcoholic beverage, a beverage comprising a dairy component and juice.

10. The method according to claim 3, wherein said article is a medicine.

11. The method according to claim 3, wherein said article is a chemical.

12. The method according to claim 3, wherein said article is a biologic.

13. The method according to claim 12, wherein said biologic is blood, an animal tissue or an organ.

14. The method according to claim 3, wherein said article is an ammunition.

15. The method according to claim 3, wherein said article is an electronic device.

16. The method according to claim 1, wherein the first alkyl ester diacetylenic acid monomer and the second alkyl ester diacetylenic acid monomer are co-crystallized at a molar ratio ranging from 1:99 to 99:1.

17. The method according to claim 1, wherein the first and second diacetylenic monomers differ from each other in monomer chain length, head-group structure, bond positioning, appendages, chirality, related features, and/or combinations thereof.

18. The method according to claim 1, wherein the co-topo-polymeric indicator composition further comprises a compound selected from the group consisting of a chromic change agent, a pigment, a nucleator and an antioxidant.

19. The method according to claim 1, wherein the co-topo-polymeric precursor composition is on a solid support.

20. The method according to claim 1, wherein the first alkyl ester diacetylenic acid monomer is a methyl ester of 10,12-heneicosadiynoic acid and the second alkyl ester diacetylenic acid monomer is a propyl ester 10,12-heneicosadiynoic acid.

21. The method according to claim 1, wherein the first alkyl ester diacetylenic acid monomer is a methyl ester of 10,12-pentacosadiynoic acid and the second alkyl ester diacetylenic acid monomer is a propyl ester of 10,12-heneicosadiynoic acid.

* * * * *